(12) United States Patent
Lane et al.

(10) Patent No.: US 9,522,964 B2
(45) Date of Patent: Dec. 20, 2016

(54) MICRONIZED STARCH AND METHODS FOR MANUFACTURING SAME

(75) Inventors: Christopher C Lane, Princeton, NJ (US); Pingyi Zhang, Belle Mead, NJ (US)

(73) Assignee: Development, Inc., Westchester, IL (US)

( * ) Notice: Subject to any disclaimer, the term of this patent is extended or adjusted under 35 U.S.C. 154(b) by 629 days.

(21) Appl. No.: 13/438,758

(22) Filed: Apr. 3, 2012

(65) Prior Publication Data

US 2013/0261195 A1 Oct. 3, 2013

(51) Int. Cl.

| | |
|---|---|
| *A61K 47/36* | (2006.01) |
| *C08B 31/00* | (2006.01) |
| *C08B 30/12* | (2006.01) |
| *A61K 9/20* | (2006.01) |
| *B29B 9/02* | (2006.01) |
| *B29B 9/12* | (2006.01) |
| *B29B 9/16* | (2006.01) |

(52) U.S. Cl.
CPC ............ *C08B 30/12* (2013.01); *A61K 9/2059* (2013.01); *A61K 47/36* (2013.01); *B29B 9/02* (2013.01); *B29B 2009/125* (2013.01); *B29B 2009/165* (2013.01); *B29B 2009/168* (2013.01); *Y10T 428/2982* (2015.01)

(58) Field of Classification Search
CPC . A37V 2250/5118; C08B 30/12; A61K 47/36; A61K 9/2059; B29B 2009/125; B29B 2009/165; C08L 3/00; C08L 3/02; A21D 2/186; B01J 2/00
See application file for complete search history.

(56) References Cited

U.S. PATENT DOCUMENTS

| | | |
|---|---|---|
| RE29,066 E | 12/1976 | Evans |
| 2004/0144206 A1 | 7/2004 | Tavares et al. |
| 2005/0002872 A1 | 1/2005 | Katz |
| 2007/0184175 A1 * | 8/2007 | Rubio et al. .................. 426/622 |
| 2007/0237730 A1 | 10/2007 | Polonka et al. |
| 2008/0029625 A1 | 2/2008 | Talton |
| 2008/0230050 A1 * | 9/2008 | Kersting et al. ................ 127/32 |
| 2008/0286410 A1 * | 11/2008 | Richmond et al. ............... 426/7 |
| 2011/0073687 A1 | 3/2011 | Kakino |

FOREIGN PATENT DOCUMENTS

| | | |
|---|---|---|
| CN | 1718589 | 1/2006 |
| CN | 101016343 A | 8/2007 |
| CN | 101880332 A | 11/2010 |
| EP | 2644622 | 10/2013 |
| JP | 2011030495 | 2/2011 |

OTHER PUBLICATIONS

Ren, G. et al., "Morphological properties and thermoanalysis of micronized cassava starch", Carbohydrate Polymers, 2010, vol. 79, Issue 1, pp. 101-105.
Wu, Q. et al., "Mechanochemical effects of micronization on enzymatic hydrolysis of corn flour", Carbohydrate Polymers, 2008, vol. 72, Issue 3, pp. 398-402.
Ren, Q. et al, "Functional Properties and Microstructure of Micronized Potato Starch", paper No. 066114, 2006 American Society of Agricultural and Biological Engineers Annual Meeting.
Che, L.-M. et al, "Micronization and Hydrophobic Modification of Cassava Starch", International Journal of Food Properties, 2007, vol. 10, Iss. 3, pp. 527-536.
Franco, C.M.L. et al., "The structure of waxy corn starch: Effect of granule size", 1998, Starch/Stärke, 50, No. 5, pp. 193-198.
Jane, J. et al., "Preparation and properties of small-particle corn starch", 1990, Cereal Chem. 69, Issue 3, pp. 280-283.
Herceg, Z. et al., "Modification of theological, thermophysical, textural and some physical properties of corn starch by tribomechanical treatment", 2010, Carbohydrate Polymers 2010, 80, Issue 4, 1072.

* cited by examiner

*Primary Examiner* — Ali Soroush
*Assistant Examiner* — Genevieve S Alley
(74) *Attorney, Agent, or Firm* — John Daniel Wood; Karen G. Kaiser

(57) ABSTRACT

The present application is related to a micronized starch with an average particle size of less than 5 μm and a degree of polymerization greater than 100, wherein the micronized starch exhibits at least 20% of the crystallinity of the base granular starch.

11 Claims, 27 Drawing Sheets

MICRONIZED STARCH AND METHODS FOR MANUFACTURING SAME

The present application is related to a micronized starch with an average particle size of less than 5 μm and a degree of polymerization greater than 100, wherein the micronized starch exhibits at least 20% of the crystallinity of the base granular starch.

Starch is a complex carbohydrate composed of two types of polysaccharide molecules: (1) amylose, a mostly linear and flexible polymer of D-anhydroglucose units that are linked by alpha-1,4-D-glucosidic bonds; and (2) amylopectin, a branched polymer of linear chains that are linked by alpha-1,6-D-glucosidic bonds. Starch has an equilibrium moisture content of 10% to 20% at normal atmospheric conditions depending on source. Cereal starches are usually about 10% to 14% moisture, while potato starch is usually about 15% to 20% moisture.

Native starches have many disadvantages for industrial applications such as insolubility in cold water, loss of viscosity, and thickening power after cooking. Starch can be physically modified to improve water solubility and to change particle size. The physical modification methods involve the treatment of native starch granules under different temperature/moisture combinations, pressure, shear, and irradiation. Physical modification also includes mechanical attrition to alter the physical size of starch granules.

Starch granules occur in all shapes and sizes (spheres, ellipsoids, polygons, platelets, irregular tubules). The long dimensions of these starch granules range from 0.1 μm to at least 200 μm, depending on the botanical source, Gallant et al. Eur. J. Clinical Nutr. 1992, 46, S3. Starch produced by wet-milling of normal corn kernels has a granular size of 5-30 μm with a reported average size of 9.2 μm, "Corn Starch, 3rd edition" Washington, D.C.: Corn Industries Research Foundation; 1964. The larger, waxy corn starch granules have X-ray diffraction patterns of the A-type, Franco et al. 1998 Starch/Stärke, 50, 193-198. Starch granules are made up of alternating amorphous and crystalline shells which are between 100 nm and 400 nm thick. X-ray diffraction shows a periodicity of 9 to 10 nm within the granules. The periodicity is due to the crystalline and amorphous thin plates in the granules and is independent of the botanical source.

Native starch granules have a crystallinity varying from 15% to 45%, Zobel Starch/Stärke, 1988, 40, 44. From the level of starch crystallinity, it is clear that most starch polymers in the granule are amorphous. Oostergetel et al. Carbohydrate Polymers, 1993, 21, 7. Most native starch granules exhibit a Maltese cross when observed under polarized light. Radial organization of amylopectin molecules within such structures causes the optical polarization. However, this birefringence remains unchanged on both polar and equatorial sections of elongated starch granules, Gallant et al. Eur. J. Clinical Nutr., 1992, 46, S3 indicating that crystallites are extremely small and exhibit multiple orientations.

Native starch granules give X-ray diffraction patterns, which lack sharp peaks. These X-ray patterns are used to identify the several allomorphs present in crystalline starch, Buleon et al. Int. J. Biol. Macromol. 1998, 23, 85. The larger A-type starch granules have a disk shape, whereas the smaller B-type starch granules have a spherical shape. Cereal starches have the A-type polymorph; tuber starches (e.g. potato) and cereal starches rich in amylose contain the B-type polymorph, and legume starches have the C-type polymorph.

The A-type starch crystal is in the monoclinic space group $B_2$ (a=2.124 nm, b=1.172 nm, c=1.069 nm, γ=123.5°) with 12 glucosyl units and 4 water molecules in the unit cell. This means the asymmetric unit contains a maltotriosyl unit, and that the packing contains one double helix at the corner and another at the center of the unit cell. The double helix is left-handed, is parallel-stranded, has a repeat distance of 2.138 nm, and is related to the other strand by a two-fold axis of rotation. The double helix is very compact, and there is no space for water in the center of the helix. There are hydrogen bonds between these helices, either direct or through the four water molecules in the unit cell.

The B-type starch crystal is in the hexagonal space group $P6_1$ (a=b=1.85 nm, c=1.04 nm). The chains in B-type starch are also organized in double helices, but the structure differs from A-type starch in crystal packing and water content, the latter ranging from 10% to 50%. Double helices are connected through a network of hydrogen bonds that form a channel inside the hexagonal arrangement of six double helices. This channel is filled with water molecules, half of which are bound to amylose by hydrogen bonds and the other half to other water molecules. Thus, with a hydration of 27%, 36 water molecules are located in the unit cell between the six double helices, creating a column of water surrounded by the hexagonal network.

Jane et al. Cereal Chem. 1990, 69, 280 reported that normal corn starch after 12 hours in a ball mill (presumably without any added solvent), "retained integrity and showed no broken pieces". If the corn starch was first subjected to acid hydrolysis under various conditions, then milled for 8 hours in a ball-mill in the presence of 100% ethyl alcohol gave between 66% and 80% yield of a small-particle starch. This small particle starch had a volume density size between 5.2±2.4 μm and 8.6±4.7 μm compared to 17.2±7.9 μm in the native starch. The small particle starch showed a strong birefringence but the Maltese cross was lost as a result of lost symmetry and spherical shape found in the native starch granules. The small particle starch produced a sharp A-type X-ray diffraction pattern with an intensity greater than seen in the native starch. This suggests that acid treatment preferentially removed the amorphous portions of the starch granule. The small particle starches of Jane et al. Cereal Chem. 1990, 69, 280 are depolymererized with an average degree of polymerization (DP) of 48.9 to 56.3.

Wu et al. Carbohydrate Polymers, 2008, 72, 398-402 prepared corn flour samples with different particle size by ball milling. A commercial corn flour with a 273.6 μm size could be micronized to 17.5 μm, 15.4 μm, 14.6 μm, 13.3 μm, and 9.8 μm in median diameter by wet-milling for 20 minutes, 1 hour, 2 hours, 3 hours, and 5 hours, respectively. Microscopic observation and X-ray diffractometry revealed the starch crystal structure of corn flour was destroyed by wet-milling for more than 3 hours.

Herceg et al. Carbohydrate Polymers 2010, 80, 1072 reports that tribomechanical micronization and activation, a process of treating solids with two closely spaced parallel discs rotating at a speed of 20,000 rpm, reduced corn starch from an average particle size of about 14 μm to about 12.5 μm. These micronized starch particles were more permeable to water, had increased water solubility, showed increased swelling power, had a lowered beginning of gelatinization temperature, and a decreased in enthalpy of gelatinization. The authors concluded, "[t]he crystalline molecular structure of corn starch is broken".

SUMMARY

In one aspect the application provides a micronized starch with an average particle size of less than 5 μm and a degree of polymerization greater than 100, wherein the micronized starch exhibits at least 20% of the crystallinity of the base granular starch.

DETAILED DESCRIPTION

Figure 1A:
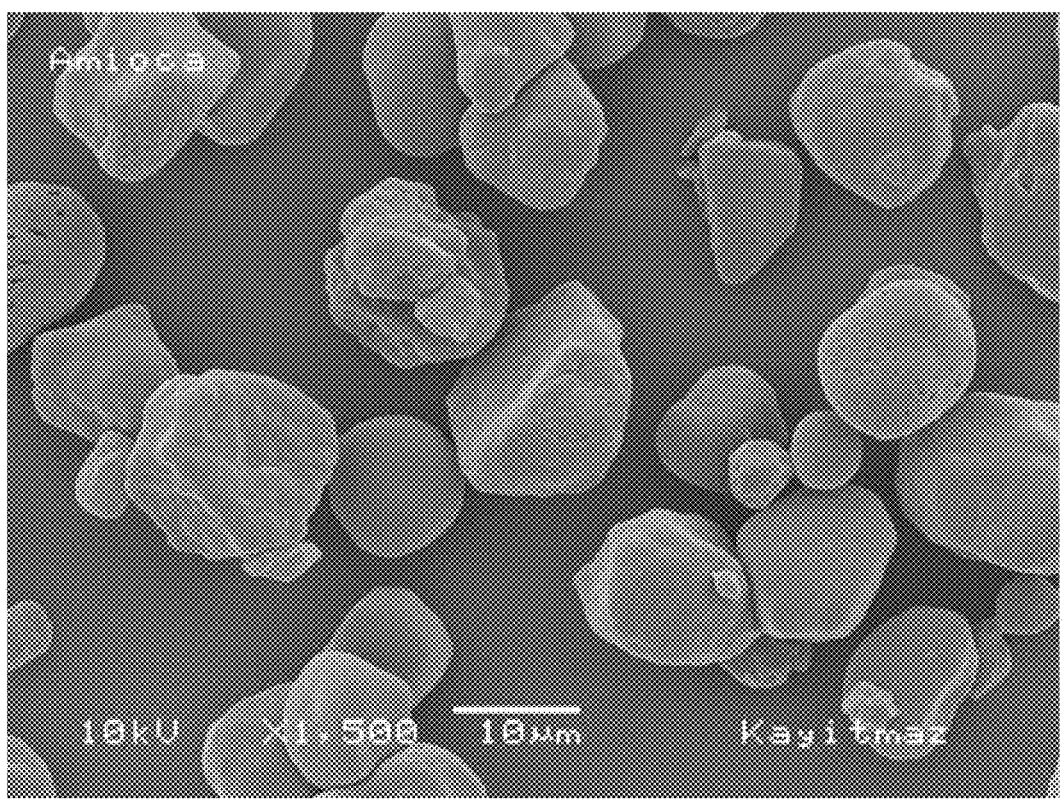
FIG. 1A depicts a scanning electron microscopy image of AMIOCA® starch granules before micronization.

In one aspect the application provides a micronized starch with an average particle size of less than 5 μm and a degree of polymerization greater than 100, wherein the micronized starch exhibits at least 20% of the crystallinity of the base granular starch.

In one embodiment, the micronized starch is produced by processing a base granular starch so as to result in a micronized starch having an average particle size at least 20% less than the average particle size of the base granular starch.

In one embodiment, the micronized starch exhibits at least 40% of the crystallinity of the base granular starch.

In one embodiment, the micronized starch exhibits at most 90% of the crystallinity of the base granular starch.

In one embodiment, the base granular starch is a cereal starch.

In one embodiment, the base granular starch is a corn starch.

In one embodiment, the melting enthalpy of the micronized starch is at least 50% of the melting enthalpy of the base granular starch.

In one embodiment, the gelatinization temperature of the micronized starch is no more than 16° C. different than the gelatinization temperature of the base granular starch.

In one embodiment, the peak viscosity of the micronized starch is not greater than 90% of the peak viscosity of the base granular starch.

In one embodiment, the degree of polymerization of the micronized starch is greater than 1,000.

In one embodiment, the degree of polymerization of the micronized starch is greater than 10,000.

In one aspect the application provides a tablet comprising the micronized starch with an average particle size of less than 5 μm, wherein the micronized starch exhibits at least 20% of the crystallinity of the base granular starch, and at least one other pharmaceutically acceptable ingredient.

In one embodiment, the tablet is characterized by a crushing strength of at least 20 PKa at a compression pressure of 3000 PSI in a tablet consisting only of the starch.

In one aspect the application provides a method of reducing starch particle size comprising the steps of:
 a) dehydrating a base granular starch to a moisture content of less than 5% on a w/w basis, and
 b) micronization of the dehydrated base granular starch in a environment containing less than 5% oxygen in a v/v basis to result in a micronized starch; wherein the micronized starch has a moisture content of no greater than 5% on a w/w basis of the base granular starch;
 wherein the micronized starch comprises an average particle size of less than 5 μm;
 wherein the degree of polymerization of the micronized starch is greater than 100; and
 wherein the micronized starch exhibits at least 20% of the crystallinity of the base granular starch.

In one embodiment, the environment containing less than 5% oxygen in a v/v basis is comprised of inert gas.

The starch of the instant application is micronized so as to result in the inventive product. Micronization can be accomplished in any manner known to one of skill in the art for particle size reduction (for example and without limitation, ball micronizing; media micronizing; fluidized bed jet micronizing; spiral jet micronizing; air classifying micronizing; universal pin micronizing; hammer and screen micronizing; attrition micronizing; cone micronizing; and/or granulating). One example of a micronization process is fluidized bed jet milling. One example of such a fluidized bed jet mill is the Hosokawa™ 100 AFG Fluidized Bed Jet Mill.

In one embodiment, base granular starch is dehydrated and then micronized under sufficient conditions so that any remaining moisture in the base granular starch is insufficient to gelatinize the starch. In another embodiment, the base granular starch is dehydrated before and/or during the micronization process so that any remaining moisture in the base starch is insufficient to gelatinize the starch during micronization. In another embodiment, base granular starch is partially dehydrated and then further dehydrated during the micronization process so that any remaining moisture in the base granular starch is insufficient to gelatinize the starch. In another embodiment, base granular starch is dehydrated during the micronization process with the use of a gas "purge" to drive off moisture contained within the base granular starch under sufficient conditions so that any remaining moisture in the base granular starch is insufficient to gelatinize the starch. In another embodiment, base granular starch is partially dehydrated and then further dehydrated during the micronization process with the use of an inert gas "purge" to drive off moisture contained within the base granular starch under sufficient conditions so that any remaining moisture in the base granular starch is insufficient to gelatinize the starch. In another embodiment, base granular starch is micronized without prior dehydration of the base granular starch and with the use of an inert gas "purge" to drive off moisture contained within the base granular starch.

In one embodiment, an inert gas "purge" is utilized during micronization to create and maintain an environment containing less than 5% oxygen in a v/v basis. In another embodiment, any type of gas can be used during micronization. Such inert gases include, but are not limited to, nitrogen, carbon dioxide, argon, or helium. In another embodiment, the dry gas has a water dew-point of about −45° C. In another embodiment, the dry gas has a water dew-point of about −65° C. In another embodiment, the dry gas has a water content less than 6 ppm. In another embodiment, the dry gas has a water content less than 1 ppm.

In one embodiment, a base granular starch is micronized in a fluidized bed jet mill in an environment containing less than 5% oxygen in a v/v basis. In another embodiment, dehydration and/or inert gas purge is utilized prior to and/or during micronization so as to remove a substantial portion of the moisture contained within the starch. In another embodiment, dehydration and/or inert gas purge is utilized prior to and/or during micronization so as to yield a micronized starch with a moisture content of not greater than about 6% immediately after micronization. In another embodiment, dehydration and/or inert gas purge is utilized prior to and/or during micronization so as to yield a micronized starch with a moisture content of not greater than about 5% on a w/w basis prior to absorption of ambient moisture. In another embodiment, dehydration and/or inert gas purge is utilized prior to and/or during micronization so as to yield a micronized starch with a moisture content of not greater than about 4% prior to absorption of ambient moisture. In another embodiment, dehydration and/or inert gas purge is utilized prior to and/or during micronization so as to yield a micronized starch with a moisture content of not greater than about 3% prior to absorption of ambient moisture. In another embodiment, dehydration and/or inert gas purge is utilized prior to and/or during micronization so as to yield a micronized starch with a moisture content of not greater than about 2% prior to absorption of ambient moisture. In another embodiment, dehydration and/or inert gas purge is utilized prior to and/or during micronization so as to yield a micronized starch with a moisture content of not greater than about 1% prior to absorption of ambient moisture.

Figure 1B:
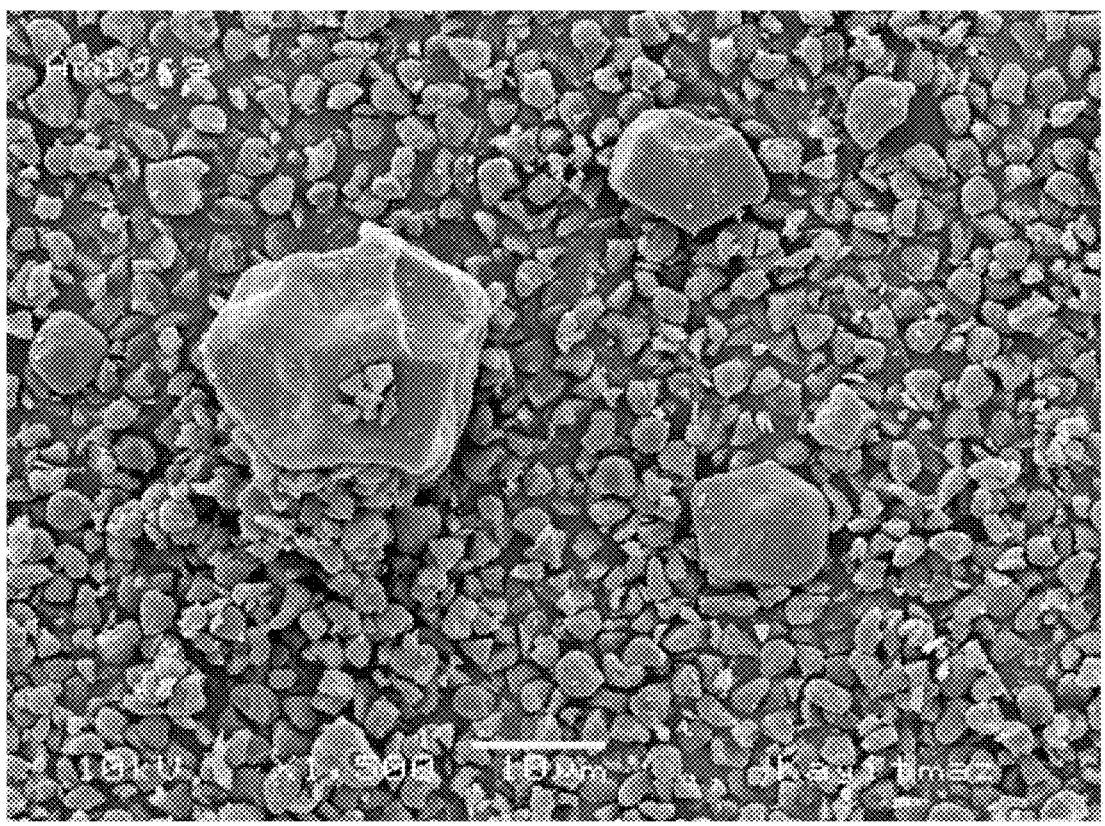
FIG. 1B depicts a scanning electron microscopy image of AMIOCA® starch granules after micronization where the granules were dehydrated prior to micronization (1B).
Figure 1C:
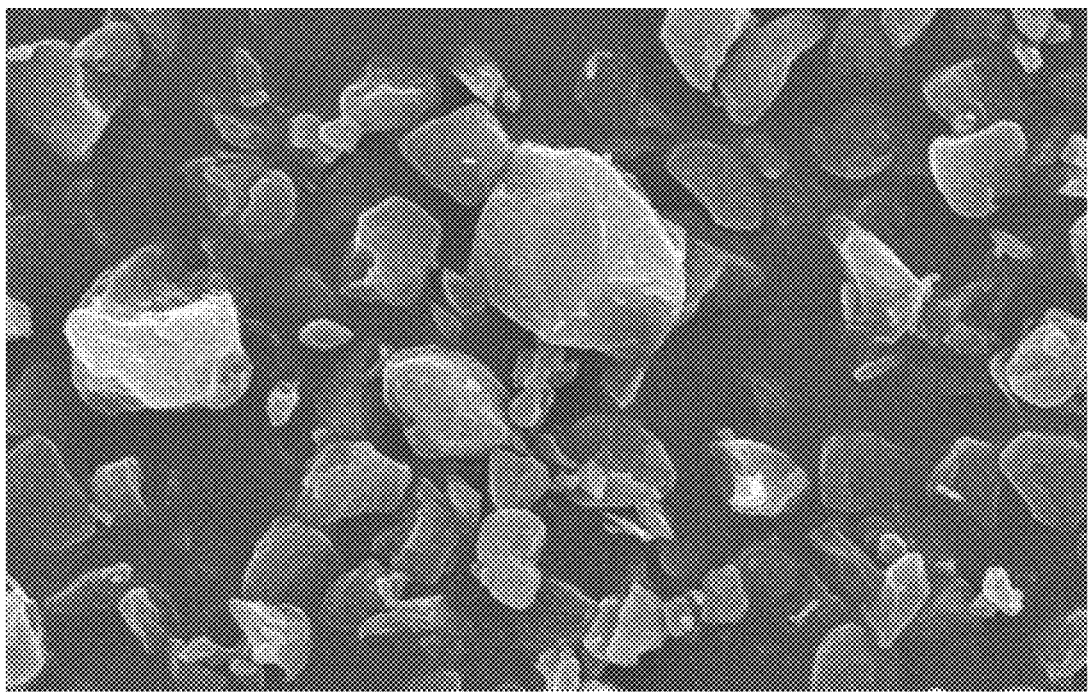
FIG. 1C depicts a scanning electron microscopy image of AMIOCA® starch granules after micronization.
Figure 2A:
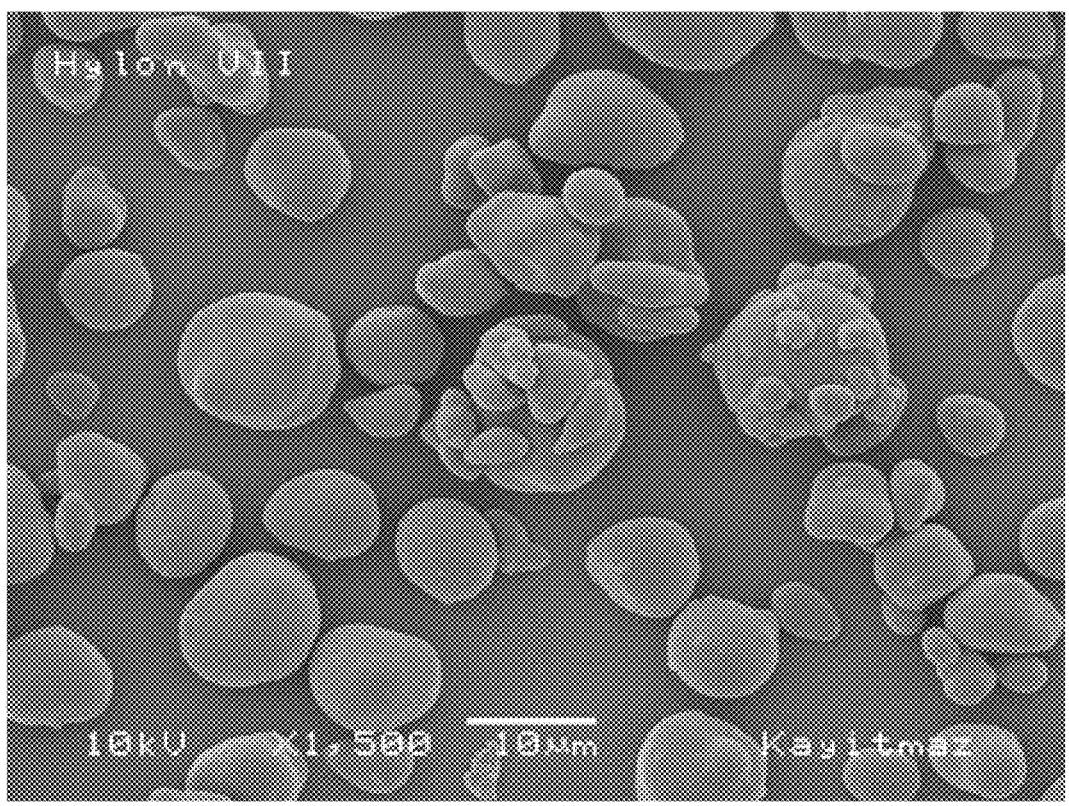
FIG. 2A depicts a scanning electron microscopy image of HYLON® VII starch granules before micronization.
Figure 2B:
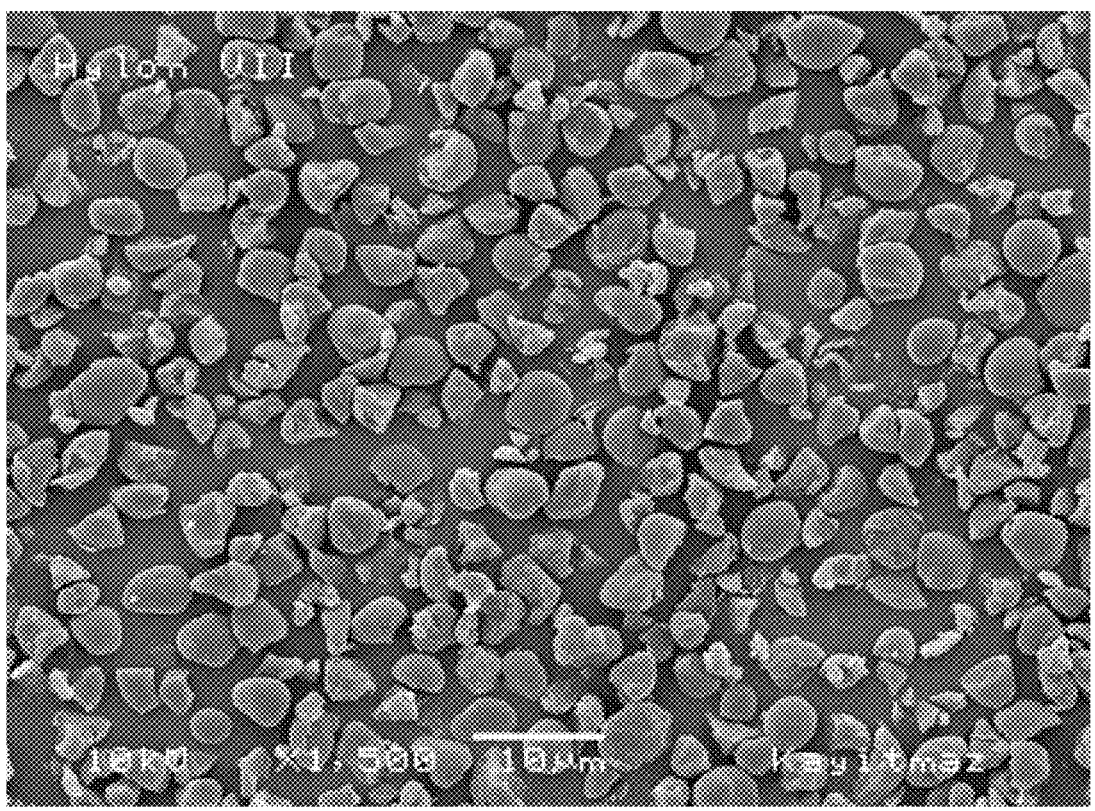
FIG. 2B depicts a scanning electron microscopy image of HYLON® VII starch granules after micronization where the granules were dehydrated prior to micronization (1B).
Figure 2C:
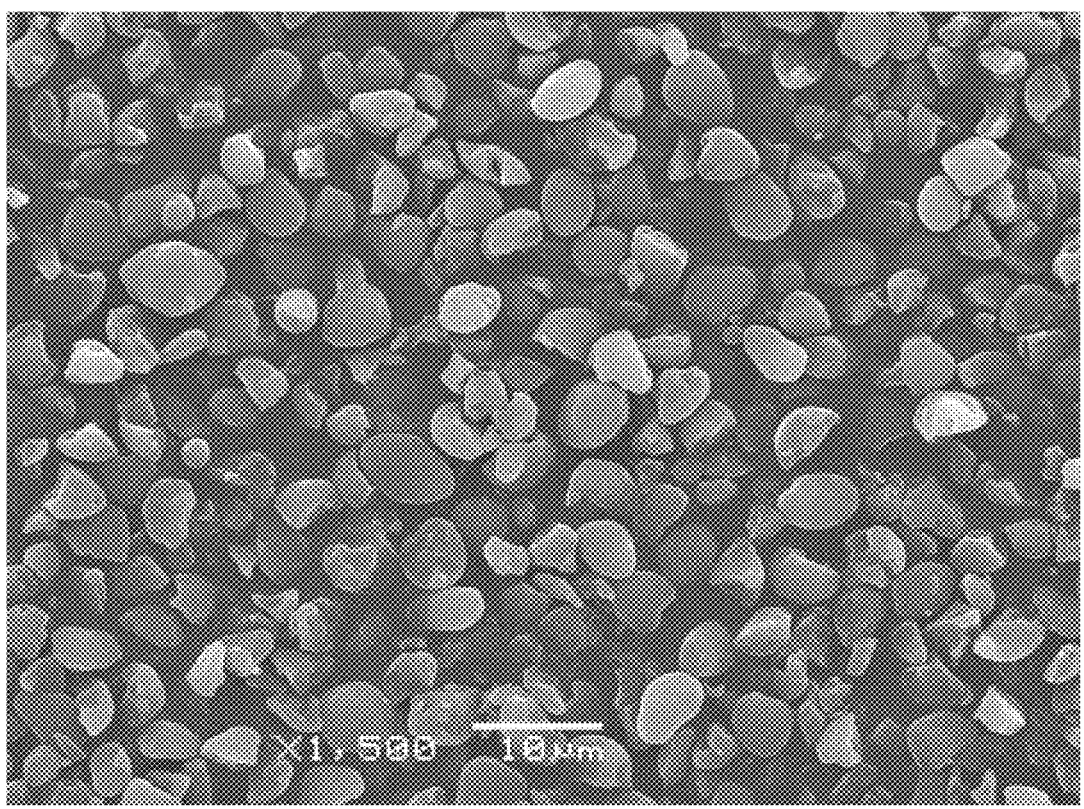
FIG. 2C depicts a scanning electron microscopy image of HYLON® VII starch granules after micronization.
Figure 3A:
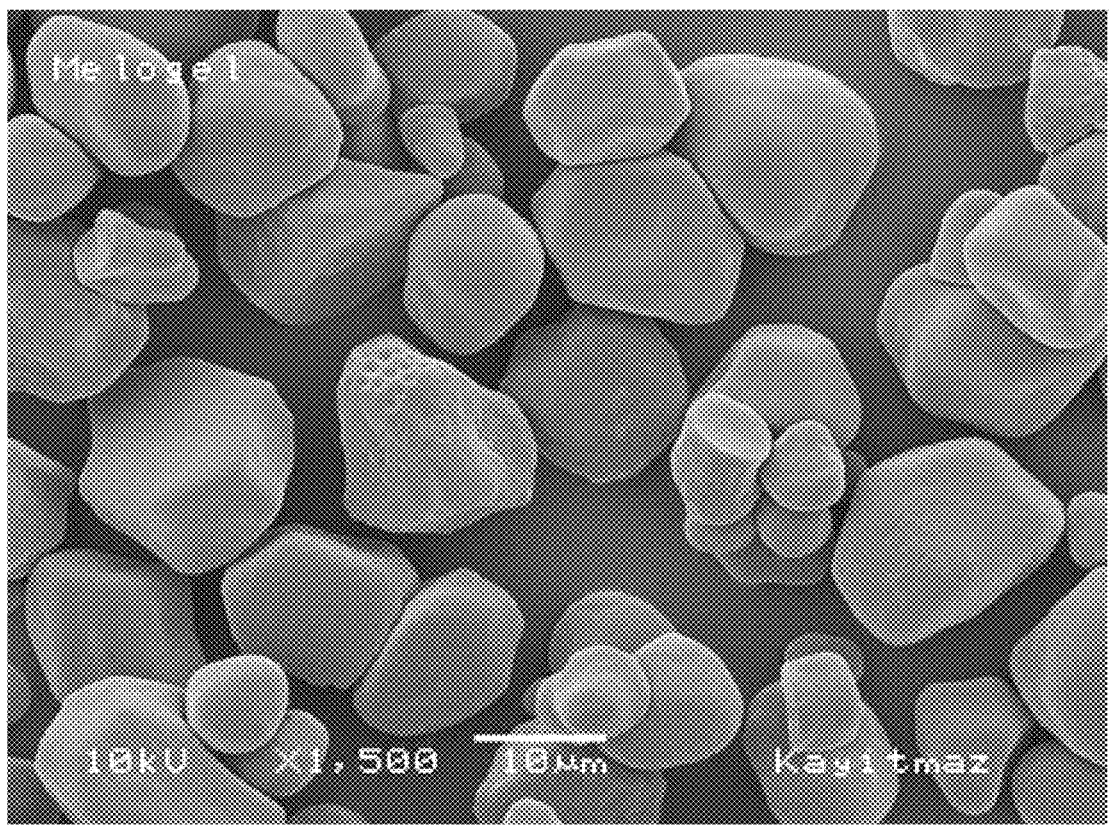
FIG. 3A depicts a scanning electron microscopy image of MELOJEL® starch granules before micronization.
Figure 3B:
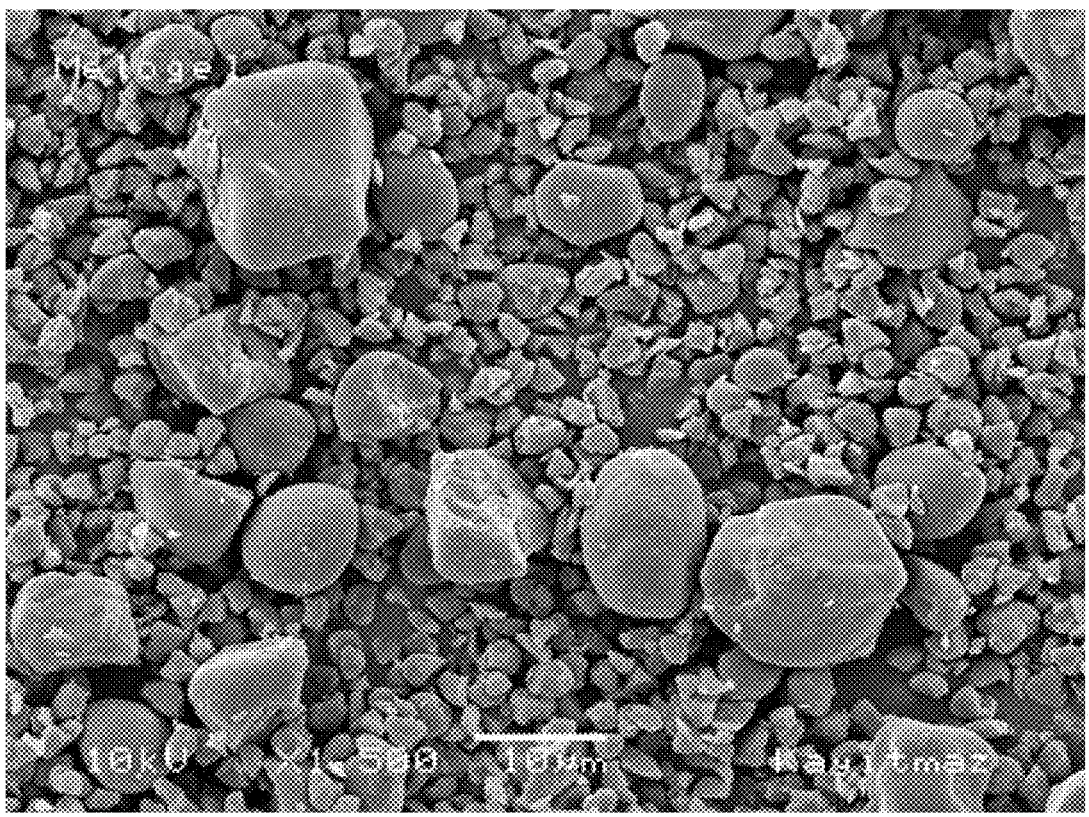
FIG. 3B depicts a scanning electron microscopy image of MELOJEL® starch granules after micronization where the granules were optionally dehydrated prior to micronization.
Figure 3C:
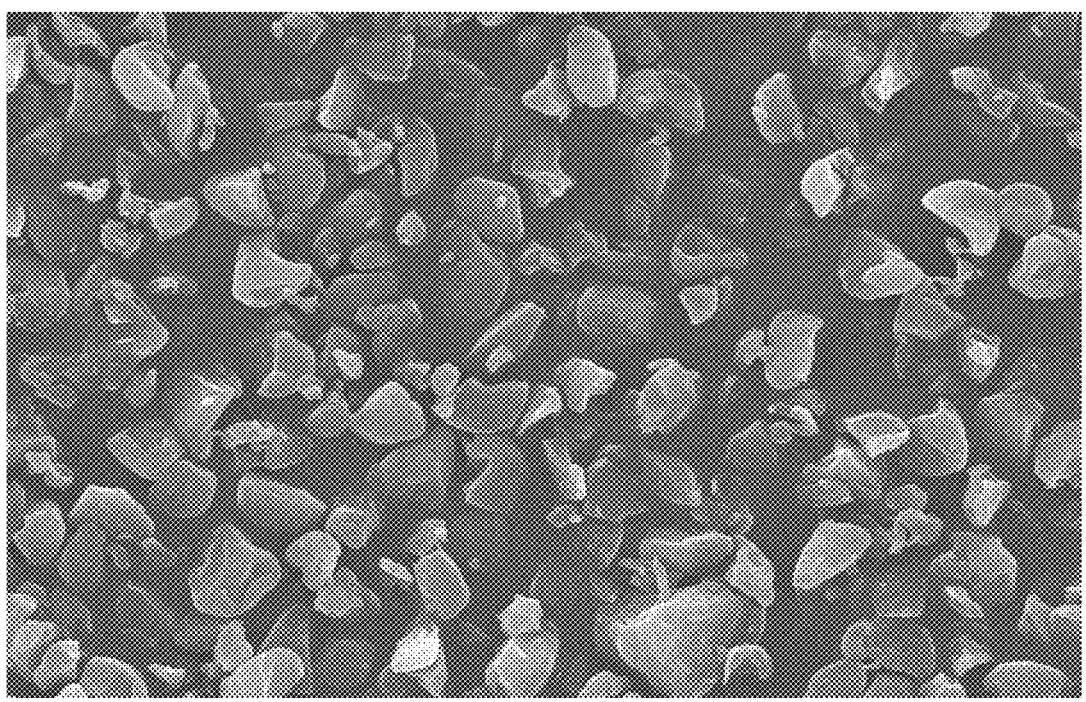
FIG. 3C depicts a scanning electron microscopy image of MELOJEL® starch granules after micronization.

FIG. 1A, FIG. 1B, and FIG. 1C (AMIOCA® starch), FIG. 2A, FIG. 2B, and FIG. 2C (HYLON® VII starch), and FIG. 3A, FIG. 3B, and FIG. 3C (MELOJEL® starch) and accompanying Examples 1 and 13 depict and describe base granular starches and micronized starches prepared in accordance with the micronization procedures discussed above.

In one embodiment, any starch may be suitable for use as a base granular starch herein and may be derived from any native starch source. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein. Typical sources for the starches are cereals, tubers, roots, legumes, or fruits. The native starch source can be sourced from any variety, including, without limitation, sourced from corn, pea, potato, sweet potato, banana, barley, wheat, rice, sago, oat, amaranth, tapioca, arrowroot, canna, sorghum, and waxy or high amylose varieties thereof. As used herein, the term "waxy" is intended to include a starch containing at least about 90%, in one embodiment at least 95%, in one embodiment at least 98, in one embodiment at least 99%, by weight amylopectin and the term "high amylose" is intended to include a starch containing at least about 40%, in one embodiment at least 50%, in one embodiment at least 70%, in one embodiment at least 80%, by weight amylose. In one aspect of this application, amylose-containing starch extracted from cereal grains, such as corn, are used. In another aspect of this application, blends of starches are used, such as a blend of corn starch and high amylose corn starch.

A base starch can be a native starch or a native starch modified by any treatment. One example of such a base starch is AMIOCA® starch. Another example of such a base starch is MELOJEL® starch. Another example of such a base starch is HYLON® VII starch.

In one embodiment, the micronized starch is modified by any number of possible treatments. In another embodiment of the present application, starch is modified by conversion. Methods of conversion are well known in the art, for example, see M. W. Rutenberg, "Starch and Its Modifications" in Handbook of Water-Soluble Gums and Resins, R. L. Davidson, editor, McGraw Hill, Inc., New York, N.Y., 1980, p. 22-36. In another embodiment of the present application, the starch is chemically modified. Chemically modified starches are intended to include, without limitation, cross-linked starches, acetylated starches, organically esterified starches, hydroxyethylated starches, hydroxypropylated starches, phosphorylated starches, inorganically esterified starches, cationic, anionic, nonionic, siliconated starches, zwitterionic starches, and succinate and substituted succinate derivatives of starch. Such modifications are known in the art, see for example in "Modified Starches: Properties and Uses." Ed. O.B. Wurzburg, CRC Press, Boca Raton, Fla., 1986. In another embodiment of the present application, the starch is physically modified. Physically modified starches, such as thermally-inhibited starches as described in Chiu et al. WO 95/04082 (A2), may also be suitable for use herein. Physically modified starches are also intended to include fractionated starches in which there is a higher proportion of amylose. In another embodiment of the present application, starch is modified by an enzyme, for example by one or more enzymes known in the art, including without limitation alpha-amylase, beta-amylase, glucoamylase, maltogenase, isoamylase, or pullulanase.

In one embodiment, the average particle size of the base granular starch is between about 5 µm and about 200 µm. In another embodiment, the average particle size of the base granular starch is at least about 5 µm. In another embodiment, the average particle size of the base granular starch is at least about 10 µm. In another embodiment, the average particle size of the base granular starch is between about 5 µm and about 20 µm. In another embodiment, the average particle size of the base granular starch is between about 5 µm and about 100 µm. In another embodiment, the mean average particle size of the micronized starch granules is between about 2 µm and about 4 µm. In another embodiment, the average particle size of the micronized starch is less than about 3 µm. In another embodiment, the average particle size of the micronized starch is less than about 2 µm. In another embodiment, the average particle size of the micronized starch is less than about 1 µm.

In one embodiment, the degree of polymerization of the micronized starch is greater than 100. In another embodiment, the degree of polymerization of the micronized starch is greater than 500. In another embodiment, the degree of polymerization of the micronized starch is greater than 1,000. In another embodiment, the degree of polymerization of the micronized starch is greater than 5,000. In another embodiment, the degree of polymerization of the micronized starch is greater than 10,000. In another embodiment, the degree of polymerization of the micronized starch is greater than 50,000.

In one embodiment, the average particle size of the micronized starch is between about 10% and about 90% of the average particle size of the base granular starch. In another embodiment, the average particle size of the micronized starch is between about 20% and about 80% of the average particle size of the base granular starch. In another embodiment, the average particle size of the micronized starch is between about 30% and about 70% less than the average particle size of the base granular starch. In another embodiment, the average particle size of the micronized starch is between about 40% and about 60% less than the average particle size of the base granular starch. In another embodiment, the average particle size of the micronized starch is no greater than about 90% of the average particle size of the base granular starch. In another embodiment, the average particle size of the micronized starch is no greater than about 80% of the average particle size of the base granular starch. In another embodiment, the average particle size of the micronized starch is no greater than about 70% of the average particle size of the base granular starch. In another embodiment, the average particle size of the micronized starch is no greater than about 60% of the average particle size of the base granular starch. In another embodiment, the average particle size of the micronized starch is no greater than about 50% of the average particle size of the base granular starch. In another embodiment, the average particle size of the micronized starch is no greater than about 40% of the average particle size of the base granular starch. In another embodiment, the average particle size of the micronized starch is no greater than about 30% of the average particle size of the base granular starch. In another embodiment, the average particle size of the micronized starch is no greater than about 20% of the average particle size of the base granular starch. In another embodiment, the average particle size of the micronized starch is no greater than about 10% of the average particle size of the base granular starch.

In one embodiment, the micronized starch exhibits at least 90% of the crystallinity of the base granular starch. In another embodiment, the micronized starch exhibits at least 80% of the crystallinity of the base granular starch. In another embodiment, the micronized starch exhibits at least 70% of the crystallinity of the base granular starch. In one embodiment, the micronized starch exhibits at least 60% of the crystallinity of the base granular starch. In one embodiment, the micronized starch exhibits at least 50% of the crystallinity of the base granular starch. In one embodiment, between 50% and 90% of the crystallinity of the base granular starch is retained in the micronized starch. In one embodiment, between 70% and 90% of the crystallinity of the base granular starch is retained in the micronized starch. In one embodiment, between 50% and 80% of the crystallinity of the base granular starch is retained in the micronized starch.

In one embodiment, retention of the crystallinity of the base granular starch in the micronized starch is assayed via X-ray diffraction. In another embodiment, the gelatinization temperature of the micronized starch is not less than 15° C. below the gelatinization temperature of the base granular starch.

In one embodiment, the melting enthalpy ($\Delta H$) of the micronized starch is no less than about 50% of the melting enthalpy ($\Delta H$) of the base granular starch. In another embodiment, the melting enthalpy ($\Delta H$) of the micronized starch is no less than about 70% of the melting enthalpy ($\Delta H$) of the base granular starch. In another embodiment, the melting enthalpy ($\Delta H$) of the micronized starch is no less than about 80% of the melting enthalpy ($\Delta H$) of the base granular starch. In one embodiment, the melting enthalpy ($\Delta H$) of the micronized starch is no less than about 90% of the melting enthalpy ($\Delta H$) of the base granular starch.

The starch composition may be used as an excipient in solid dosage forms, including without limitation, capsules, caplets, and tablets. The particle size and moisture content of the micronized starch composition will affect the flowability, density, compressibility, binding, and disintegration properties. The starch composition may be incorporated into a solid dosage form using methods known in the art.

In one embodiment, the starch composition is mixed with the active agent and filled into a capsule. In another embodiment, the micronized starch composition is incorporated using direct compression.

The micronized starch composition may be used as a pharmaceutical excipient, such as a binder, a disintegrant, a filler, or to serve the multiple purpose of any combination of these functionalities (e.g. as a binder-disintegrant). In one embodiment, the micronized starch of the present application is utilized in the preparation of clinical nutrition products and as a source of enriched fiber for same. In another embodiment, the micronized starch of the instant application is utilized for manufacture of clinical nutrition products, and the material of the present application may be characterized by a predominance of micronized starch particles measuring between 1 μm and 5 μm in particle size. In another embodiment, the micronized starch of the present application may be utilized to provide a smooth mouth feel and desired texture for clinical nutrition products. In another embodiment, the micronized starch of the present application may be utilized to form a colloidal (creamy) system in the context of a clinical nutrition product for hours without precipitation. In another embodiment, the micronized starch of the present application may be utilized to form a colloidal (creamy) system that can stand overnight without separation. In another embodiment, the micronized starch of the present application may be utilized as a fat replacer. In one embodiment, the micronized starch of the present application may be utilized as a thickener. In one embodiment, the micronized starch of the present application may be utilized as a rheology modifier. In one embodiment, the micronized starch of the present application may be utilized as a component of a colloidal system. In one embodiment, the micronized starch of the present application may be utilized as a microcrystalline cellulose (MCC) replacement as a binder or otherwise as a pharmaceutical excipient.

DEFINITIONS

The following definitions are used in connection with the present application unless the context indicates otherwise. All parts and percentages are given by weight and all temperatures in degrees Centigrade (° C.) unless otherwise indicated. All percents used are on a weight/weight basis. Unless otherwise specified, all percentages expressed herein are weight/weight. Drierite® is a desiccants made from anhydrous calcium sulfate (gypsum). Some varieties contain 3% cobalt (II) chloride, a moisture-sensitive color indicator that shows when that material's activity has been depleted. Drierite® is a registered trademark of the W.A. Hammond Drierite Co., Ltd., Xenia, Ohio.

The term "average particle size" means the mean particle size of a composition of a plurality of particles, as assessed by Polarization Intensity Differential Plus Electric Light Scattering, in accordance with Example 8 herein.

The term "base starch" means a starch obtained from the same plant source as a corresponding micronized starch that has been processed in the same manner but has not been reduced in average particle size.

The term "crushing strength" means the force necessary to fragment a dosage form, in accordance with Example 10 herein.

The term "comminuting" means a method of reducing the average particle size of a material.

The term "compression pressure" means pressure utilized to compress a sample into tablet form, measured in Newtons.

The term "crystallinity" means the degree of structural order in a solid. Many materials can be prepared in such a way as to produce a mixture of crystalline and amorphous regions. In such cases, crystallinity is usually specified as a percentage of the volume of the material that is crystalline. Crystallinity can be measured using X-ray diffraction. The percent of crystallinity as assessed by X-ray diffraction and in accordance with Example 3 herein.

The term "degree of polymerization" or "DP" means the number of D-anhydroglucose units in a starch molecule.

The term "dehydrating starch to a moisture content" means reducing the moisture content in a starch.

The term "gelatinized" means that a starch is no longer a granular starch as defined herein.

The term "gelatinization temperature" means the onset temperature of gelatinization measured in accordance with Example 6 herein.

The term "granular starch" means raw uncooked starch, i.e., starch in its natural form found in cereal, tubers, or grains. Starch is formed in plants as tiny granules insoluble in water.

These granules are preserved in starches at temperatures below the initial gelatinization temperature. When put in cold water, the grains may absorb a small amount of the liquid. Up to 50° C. to 70° C. the swelling is reversible, the degree of reversibility being dependent upon the particular starch. With higher temperatures an irreversible swelling called gelatinization begins.

The term "melting enthalpy" ($\Delta H$) means the amount of heat required to convert a unit mass of a solid at its melting point into a liquid without an increase in temperature, as assessed utilizing differential scanning calorimetry in accordance with Example 6 herein.

The term "micronized" means comminuted so as to reduce the average size of a solid material's particles. Usually, the term micronization is used when the particles that are produced are only a few micrometers (μm) in diameter. Micronization can be achieved by processes including, but not limited to, jet milling, pearl-ball milling, high-pressure homogenization, the RESS process (Rapid Expansion of Supercritical Solutions), the SAS method (Supercritical Anti-Solvent), or the PGSS method (Particles from Gas Saturated Solutions).

The term "moisture content" means the moisture content as measured in accordance with Example 2 herein.

The term "substantially oxygen-free environment" means an ambient environment having less than about 5% oxygen by volume.

Certain specific aspects and embodiments of the present application are explained in more detail with reference to the following examples, which are provided only for purposes of illustration and should not be construed as limiting the scope of the application in any manner.

EXAMPLES

Example 1A

Manufacture of a Dry-Ground, Micronized Starch

A base granular starch was dehydrated, prior to micronization of the base granular starch, to a moisture less than about 5% on a w/w basis. The base granular starch was manually charged into the hopper, which conveys material to the grind chamber by a screw feeder. The base granular starch was milled under substantially oxygen free conditions created by the use of an inert gas "purge" of the mill during the micronization process to drive off excess moisture. The base granular starch was milled using a Hosokawa® 100 AFG Fluidized Bed Jet Mill (20 lbs. capacity) so as to result in a micronized base granular starch.

1B Dehydration and Micronized of the Base Granular Starch so that any Remaining Moisture in the Base Granular Starch is Insufficient to Gelatinize the Starch The base granular starch was dehydrated to a moisture of less than about 5% on a w/w basis prior to micronization.

The dehydrated base granular starch was then milled using a Hosokawa™ 100 AFG Fluidized Bed Jet Mill (20 lbs. capacity) so as to result in a micronized base granular starch using nitrogen gas to create substantially oxygen free conditions in the mill during the micronization process to drive off excess moisture.

1C Dehydration of the Base Granular Starch During the Micronization Process so that any Remaining Moisture in the Base Granular Starch is Insufficient to Gelatinize the Starch The base granular starch was milled using a Hosokawa™ 100 AFG Fluidized Bed Jet Mill (20 lbs. capacity) so as to result in a micronized base granular starch. The base granular starch is not dehydrated prior to the micronization step.

1D Partial Dehydration of the Base Granular Starch and then Further Dehydration During the Micronization Process so that any Remaining Moisture in the Base Granular Starch is Insufficient to Gelatinize the Starch The base granular starch was partially dehydrated prior to micronization the base granular starch to a moisture of less than about 5% on a w/w basis. The dehydrated base granular starch was then milled using a 100 AFG Fluidized Bed Jet Mill (20 lbs. capacity) so as to result in a micronized base granular starch. Nitrogen was utilized to create a substantially oxygen free conditions in the mill during the micronization process to drive off excess moisture.

1E Dehydration of the Base Granular Starch During the Micronization Process with the Use of an Inert Gas "Purge" to Drive Off Moisture Contained within the Base Granular Starch so that any Remaining Moisture in the Base Granular Starch is Insufficient to Gelatinize the Starch as a Result of the Heating of the Starch (Through Friction and/or Other Means) During the Micronization Process Nitrogen is utilized to create a substantially oxygen free condition in a Hosokawa™ 100 AFG Fluidized Bed Jet Mill (20 lbs. capacity) during the micronization process to drive off excess moisture.

1F Oven Drying of the Base Granular Starch Prior to Micronization, without the Use of a Subsequent Inert Gas "Purge" to Drive Off Moisture Contained within the Base Granular Starch The base granular starch was dehydrated prior to micronization the base granular starch to a moisture less than about 5% on a w/w basis. The dehydrated base granular starch with low moisture was then milled using a Hosokawa™ 100 AFG Fluidized Bed Jet Mill (20 lbs. capacity) so as to result in a micronized base granular starch.

Example 2

Determining and Measuring Moisture of Micronized Starch

Moisture in a starch or dextrin sample is determined by heating a known quantity of sample for 4-6 hours at 130±2° C. in a gravity convection oven. Oven moisture determinations may be done on most starch and dextrin products. This method measures the amount of volatiles lost after heating. For test purposes, these volatiles are considered water. This method is also referred to as Loss on Drying. The equipment needed includes: (1) analytical balance, capable of 0.0001 gram accuracy; (2) aluminum moisture dishes with covers, approximately×15 mm (Fisher Scientific #08-722 or equivalent); (3) oven, gravity convection, maintained at 130±2° degrees C.; (4) desiccators with indicating Drierite® (anhydrous $CaSO_4$) or other suitable desiccant; (5) crucible tongs, general purpose, approx. 9"; (6) small laboratory spatula or sponula. Several aluminum weighing dishes are conditioned in a 130±2° C. oven for 2 to 3 hours (number the tops and bottoms of each weighing dish before conditioning). Using a pair of tongs, the conditioned aluminum weighing dishes are then removed from the oven and placed in a desiccator containing suitable desiccant. The conditioned aluminum weighting dishes are allowed to cool for 30-60 minutes. In duplicate, using an analytical balance, the weight of an oven dried aluminum weighing dish and lid is obtained and recorded as "A". A 4-5 gram portion of the sample is transferred to the weighing dish. The dish is immediately covered and weighed. This weight is recorded as "B". The dish is placed, uncovered, in a 130±-2° C. oven for 4-6 hours. The dish is removed from the oven, immediately covered with the top, and placed into a desiccator. The dish is allowed to cool for 15-30 minutes. The dish is removed from the desiccator and accurately weighed. This weight is recorded as "C". Moisture content is calculated and reported to one decimal place in accordance with the following equation:

$$\% \text{ moisture} = (100 - (C-A) \times 100)/(B-A)$$

(B–A)=sample weight before drying (C–A)=remaining residue weight after drying for four hours.

Alternately, an inert gas "purge" may be introduced into the micronization process so as to drive off moisture contained within the base granular starch so that any remaining moisture in the base granular starch is insufficient to gelatinize the starch. The moisture of the inert gas prior to and subsequent to introduction of the inert gas into the micronization apparatus may be compared so as to determine the degree to which the moisture of the micronized starch was reduced in producing the micronized starch.

Example 3

Measuring Crystallization of Micronized Starches by X-Ray Diffraction

Starches are measured by powder X-Ray diffraction. X-ray diffraction patterns are obtained with an X-ray diffractometer (Rigaku Miniflex) equipped with a sealed X-ray tube with Cu $K_\alpha$ radiation (A=1.5418 Å). The diffractometer is operated at 15 mA and 30 kV, and the spectra are scanned over a diffraction angle (28) range of 10° to 40° at a step size of 0.1° and a count time of 0.5 seconds. Crystallinity is calculated as the percentage of peak area to the total diffraction area.

Example 4

Figure 4:
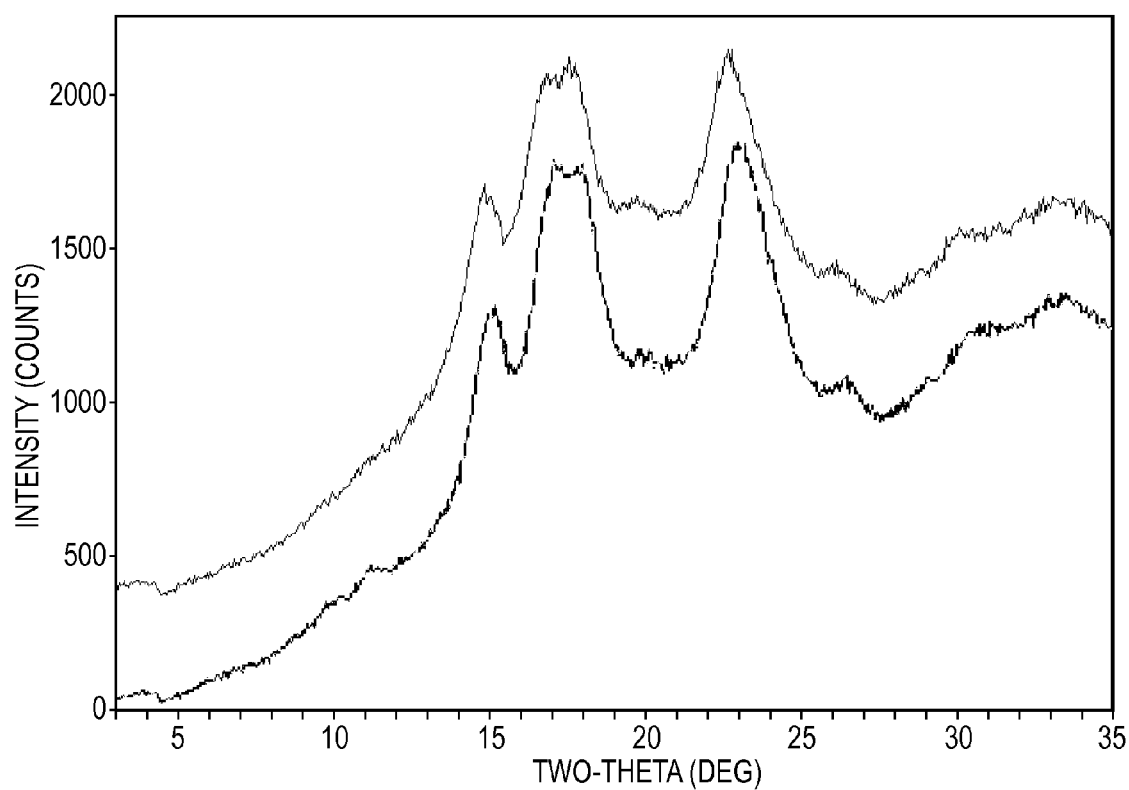
FIG. 4 depicts X-ray diffraction analysis of crystallinity of base granular and micronized AMIOCA® starch.
Figure 5:
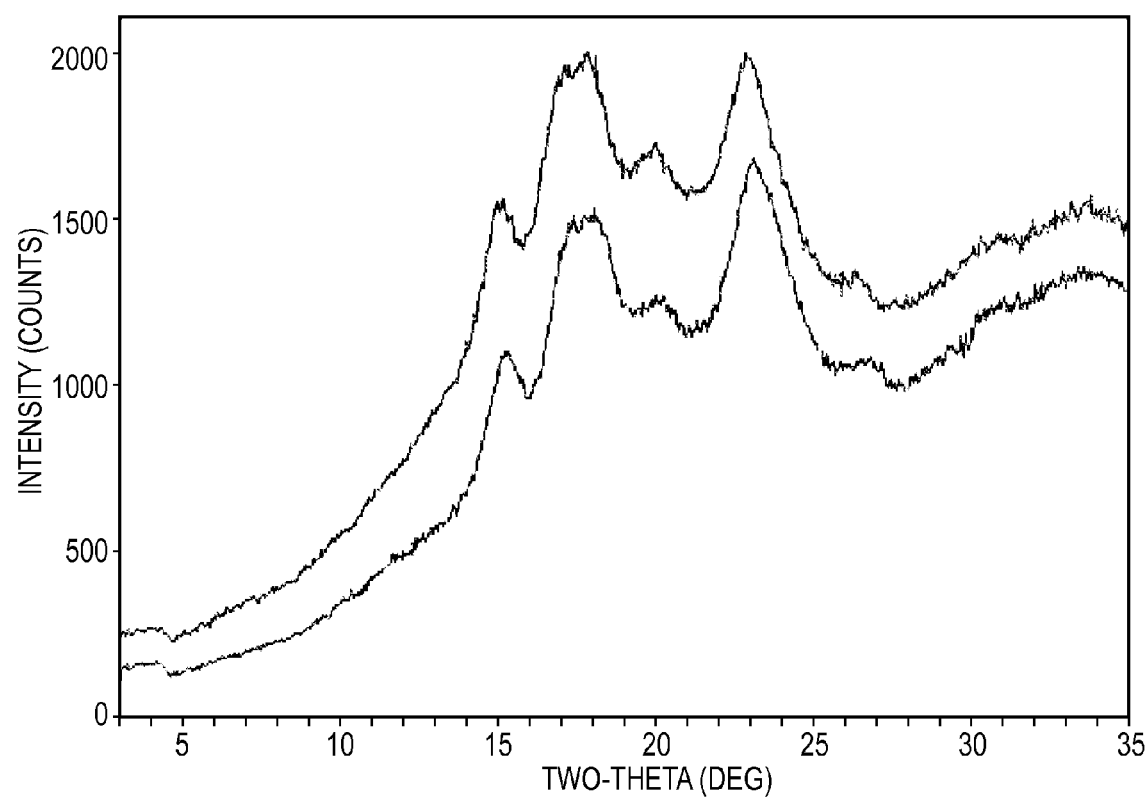
FIG. 5 depicts X-ray diffraction analysis of crystallinity of base granular and micronized MELOJEL® starch.
Figure 6:
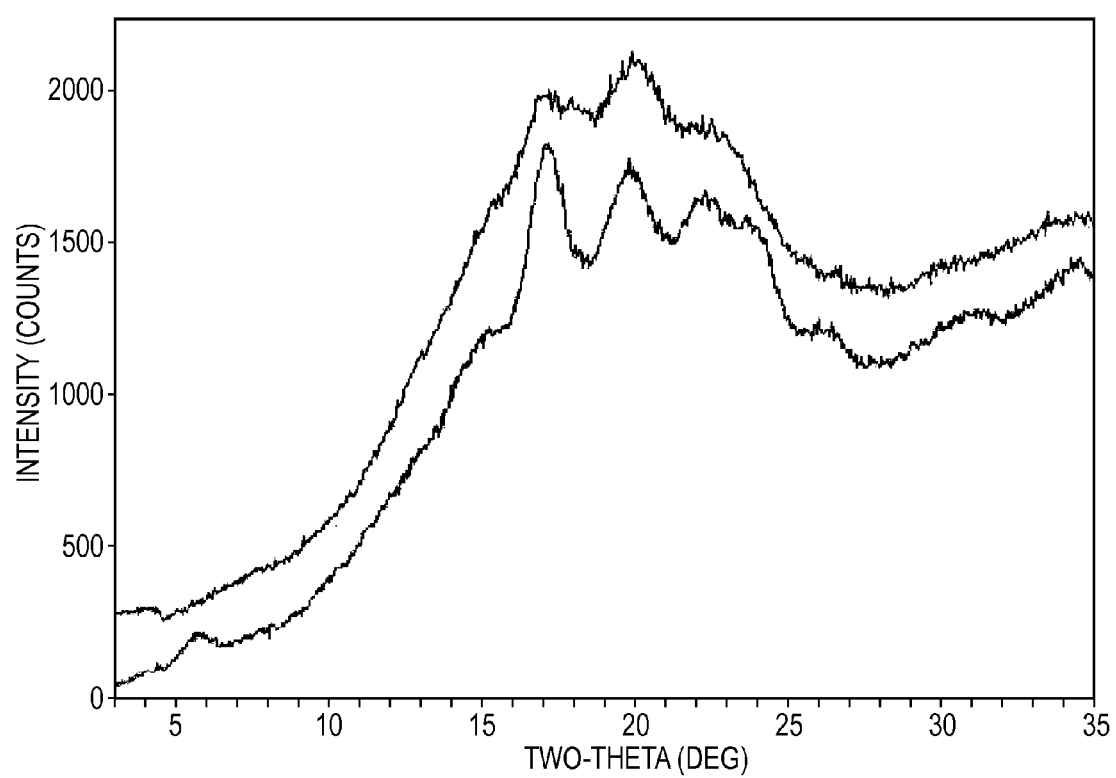
FIG. 6 depicts X-ray diffraction analysis of crystallinity of base granular and micronized HYLON® VII starch.

Measuring Crystallization of Micronized Starches by Retention of Birefringence The morphology of this partially pregelatinized starch composition is observed using scanning electron microscope (SEM) (FIG. 1A-3C); and X-ray diffraction (FIG. 4-6). For microscopic analysis, approximately 0.5% starch powder is dispersed in water homogeneously and observed using a microscope under both light and polarized light. For SEM analysis, samples are mounted and vacuum-coated with gold. The SEM analysis is performed at 15 kV with a beam current of $2\times10^{-10}$ A. The distance to sample is set at 15 mm to achieve good image quality.

Example 5

Measuring Gelatinization Temperatures of Micronized Starches

Small particles of the starch are placed between a slide and cover slip and the sample is heated and cooled while being examined for its crystal structure. A small amount of the starch is dispersed in deionized water, placed on a glass slide, and covered with a cover slip. This sample is then heated from room temperature to 100° C. at a rate of 5° C. per minute using a Mettler Hot Stage in conjunction with the use of an Olympus Polarized Light Microscope fitted with a long working distance objective. Images are collected at specified intervals during the experiment to document the changes to the starch granules as the sample is heated. The gelatinization temperature is determined by observing the swelling of the starch granules. This results in a temperature range with an onset of gelatinization where granules are first observed to swell and a completion of gelatinization where no more swelling of the granules is observed.

Example 6

Measuring (Heat of Enthalpy) Temperatures of Micronized Starches

Differential scanning calorimetry (DSC) measurements are performed in a Perkin-Elmer DSC-7 (Norwalk, Conn., U.S.A). The instrument was calibrated with indium. Samples of approximately 10 mg starch at a starch:water ratio of 1:3 are prepared and heated at 10° C./min from 50° C. to 160° C. An empty stainless steel pan was used as a reference.

Example 7

Figure 13:
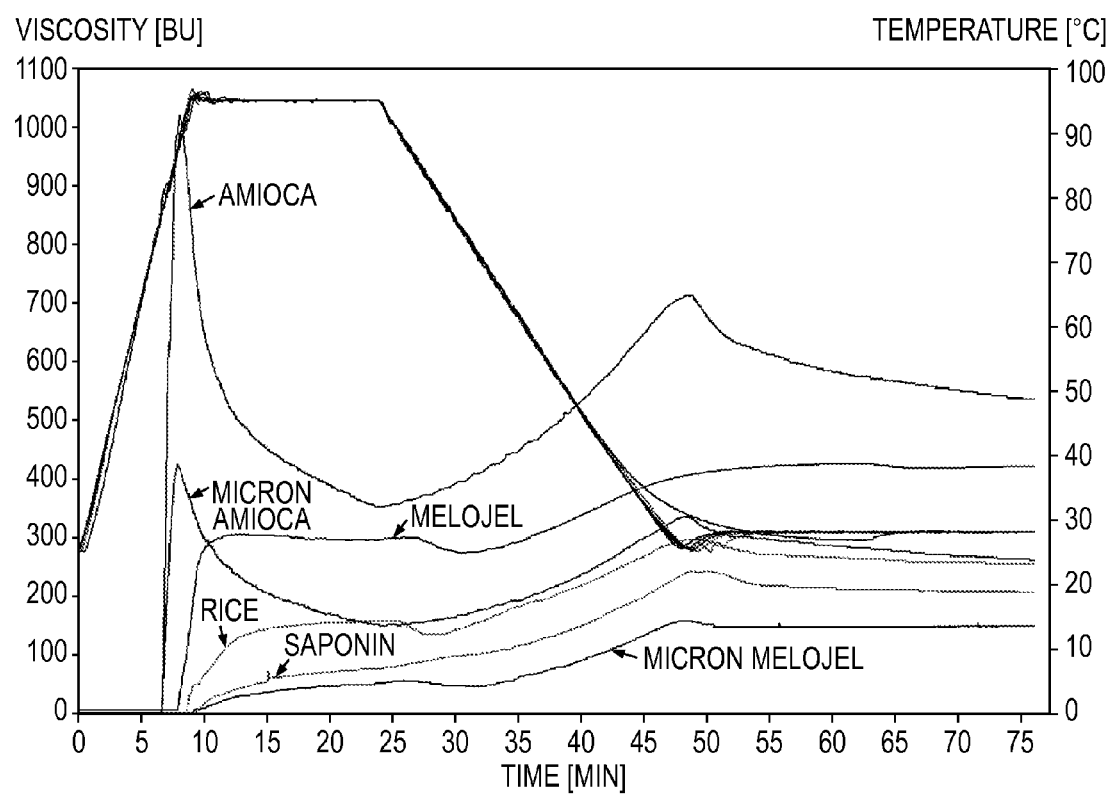
FIG. 13 depicts Brabender viscosity curve results obtained from base granular and micronized AMIOCA® starch and MELOJEL® starch as well as rice and saponin.

Measuring Peak Viscosity of Starches Utilizing a Brabender Viscometer at Neutral pH The peak viscosity of the starch of the instant application is determined using a Brabender viscoamylograph. A 97.4 g portion of the starch is mixed with 389.6 g of distilled water and added to the Brabender viscoamylograph bowl. The slurry is heated from 25° C. to 92° C. at a rate of 4° C./minute and held at 92° C. for twenty minutes. The slurry is then cooled to 25° C. at a rate of 1.5° C./minute. The results are shown in FIG. 13.

Example 8

Measuring Particle Size and Distribution of Micronized Starches

Particle size is measured using a LS 13 230, manufactured by Beckman Coulter (Indianapolis, Ind.) and incorporating Polarization Intensity Differential Screening (PIDS) technology together with a software package to provide a dynamic range of particle size measurement capabilities from 0.04 µm to 2000 µm. From the pull down manual of the software, the sample ID is entered the appropriate optical module to be used for the system to be measured is selected. A sequence of steps automatically follows: measuring offsets; alignment; background measurement; and measure loading. The instrument sounds a bell and displays measuring loading when ready to accept a sample. A diluted (approximately 1% solids) sample is introduced by drops into the sample reservoir and the changes in the measure loading are observed. This function measures the amount of light scattered out of the beam by the particles so as to determine an appropriate concentration of sample. When sizing particles without using PIDS an obscuration level of 8% to 12% is appropriate. When PIDS is used, a PIDS obscuration of 40% to 60% is recommended. A real part of index of refraction of 1.5 was used.

Example 9

Manufacture of a Micronized Starch-Containing Tablet

Formulations containing active ingredients were prepared for direct compression. The active ingredient, starch composition, and other ingredients (except lubricant) were mixed in a Turbula (Willy A. Bachofen AG Maschininfabrik, Switzerland, Type T2F) mixer for 15 minutes. The mixture was sieved through a 40 mesh (425 µm) sieve and the fraction passing through the screen is used. Lubricant was then added and the blend was mixed for another 1 to about 2 minutes. After mixing, the powders were stored in airtight containers until made into tablets. A single punch tablet press (Globe Pharma Model MTCM-1). Placebo starch tablets (containing 100% starch) were produced by this method. The single station tablet press was fitted with a 1.11 cm (7/16") standard concave punch and a corresponding die. A 500 mg portion of the powder was weighed (1% accuracy), fed into the die cavity, and compressed at 13 kN compression force. The compression time took about two to three seconds.

Example 10

Evaluation of Crushing Strength

Tablet hardness, indicated as tablet crushing strength, was determined for ten tablets, prepared using a Pharmatron (Model 6D) tablet tester. All tablets were prepared using 600 mg of powder on the single station tablet press, model MTCM-I (Globe Pharma, Inc.) at 13.7 MPa compression force and using a ½ inch die cavity. The tablet press was fitted with 1.27 cm particle size punch die. Tablet crushing strength was measured on a Dr. Scheuniger Pharmatron Model 6D Tablet Tester (Pharmatron AG, Switzerland). Three tablets were tested from each sample.

Example 11

Preparation of a Colloid with a Micronized Starch

Micronized starch (approximately 5 g) was gradually added into water (100 g) while agitating using a stirring bar for 5 to 15 minutes. After the micronized starch powder was fully dispersed, a colloidal system was formed which was milky and smooth in texture. This was designated as a colloidal stock. Approximately 10 mL of the colloidal stock was then mixed with Yoplait® yogurt (100 mL, General Mills, Minneapolis, Minn.) to form a colloidal dispersion.

Example 12

Evaluation of Colloid Stability

Micronized starch (approximately 5 g) is gradually added into water (100 g) while agitating using a stirring bar for 5 to 15 minutes. After micronized starch powder was fully dispersed a colloidal system was formed which was milky and smooth in texture, designated as a colloidal stock. Approximately 10 mL of the colloidal stock was then mixed with Yoplait® yogurt (100 mL, General Mills, Minneapolis, Minn.) to form a colloidal dispersion. Using micronized Hi-Maize® starch, micronized NOVELOSE® 330 starch, or micronized NOVELOSE® 480HA starch, potential dietary fiber formulations were obtained. Formulations are evaluated and stored in refrigerator at 4° C. Results showed that formulations were smooth in texture and stable maintaining integrity and texture after 5 days without separation, while control formulations with non-micronized starches separated overnight.

Example 13

Preparation of Micronized AMIOCA® Starch, Micronized HYLON® VII Commercial High Amylose Corn Starch, or Micronized MELOJEL® Dent Corn Starch Dry grinding using an 100 AFG Fluidized Bed Jet Mill (20 lbs. capacity) was carried out at Pharmaceutical and Food Division, Hosokawa Micron Powder Systems, Summit, N.J. Samples of AMIOCA® starch, HYLON® VII starch, and MELOJEL® starch (FHI 0363), were procured. Each sample was divided further into an "oven dried" and an "as is" sample. The "oven dried" samples of AMIOCA® starch, HYLON® VII starch, and MELOJEL® starch were dehydrated prior to micronization. The "as is" samples of AMIOCA® starch, HYLON® VII starch, and MELOJEL® starch were not dehydrated prior to micronization. Each of the 6 samples (AMIOCA® starch, HYLON® VII starch, and MELOJEL® starch, in "oven dried" and "as is" form) were then jet-milled. A sufficient amount of dry nitrogen gas was utilized during jet milling, both to maintain a substantially oxygen-free environment during the jet milling process, and to drive off excess moisture liberated during the jet milling process itself and thereby substantially prevent gelatinization of the starch samples during the jet milling process. TABLE 1, reprinted below, provides a summary of the sizes and crystallinity of (a) base AMIOCA® starch, MELOJEL® starch, and (b) "as-is" jet-milled AMIOCA® starch, MELOJEL® starch, and HYLON® VII starch; and (c) "oven dried" AMIOCA® starch, MELOJEL® starch, and HYLON® VII starch.

TABLE 1

| Starch | Average Particle Size Pre-Micronization (μm) | Average Particle Size Post-Micronization (μm) | Micronized Crystallinity (%) |
|---|---|---|---|
| AMIOCA® Starch | 14.4 | 2.7 | 31.0 |
| MELOJEL® Starch | 18.3 | 3.4 | 27.4 |
| HYLON® VII Starch | 11.4 | 3.7 | 20.0 |

Example 14

Retention of Crystallinity in Micronized Starches as Measured by X-Ray Diffraction Analysis Using the analytical procedure of Example 3, micronized AMIOCA® starch (FIG. 4), micronized HYLON® VII starch (FIG. 5), and micronized MELOJEL® starch FIG. 6), retain most of the crystallinity of the granular starches from which they are derived, utilizing the micronized starches were produced in accordance with Example 13. Data summarizing crystallinity analysis is summarized in Table 2 below.

TABLE 2

| Starch | Native Crystallinity (%) | Micronized Crystallinity (%) | Retention of Crystallinity (%) |
|---|---|---|---|
| AMIOCA® starch | 38.6 | 31.0 | 80.3 |
| MELOJEL® starch | 37.5 | 27.4 | 73.0 |
| HYLON® VII starch | 27.5 | 20.0 | 72.5 |

Example 15

Figure 7A:
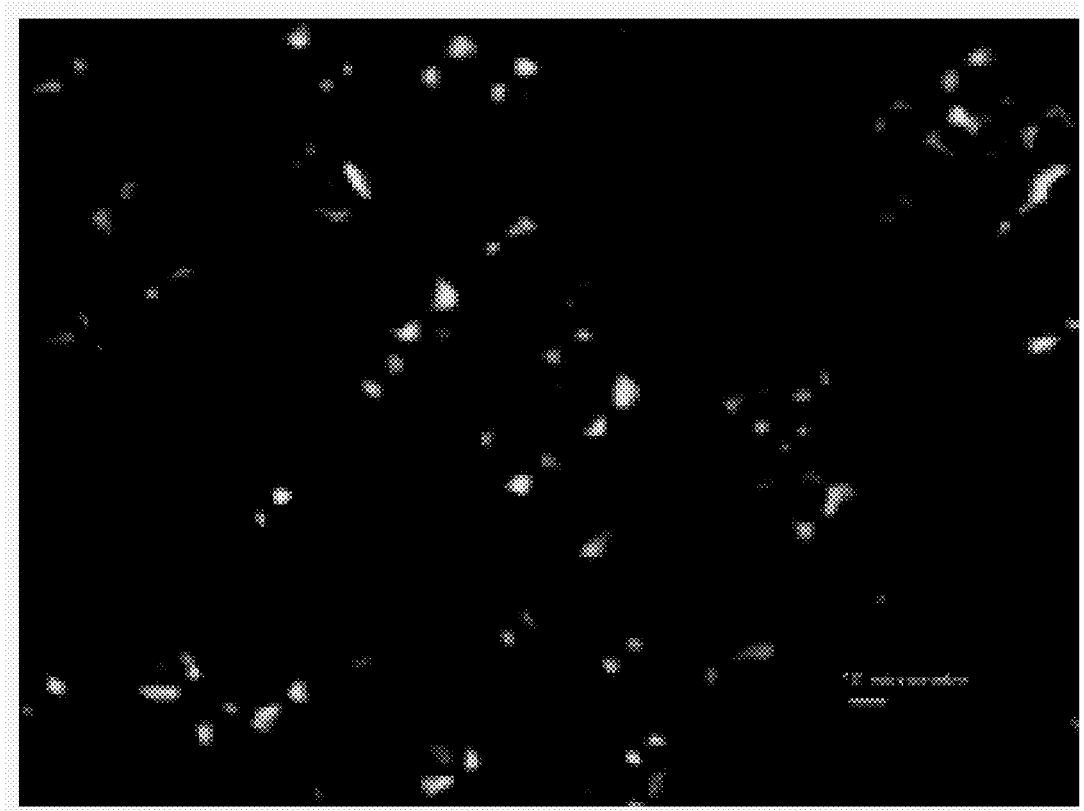
FIG. 7A depicts polarized light microscopy (400×) photographs of base granular AMIOCA® starch.
Figure 7B:
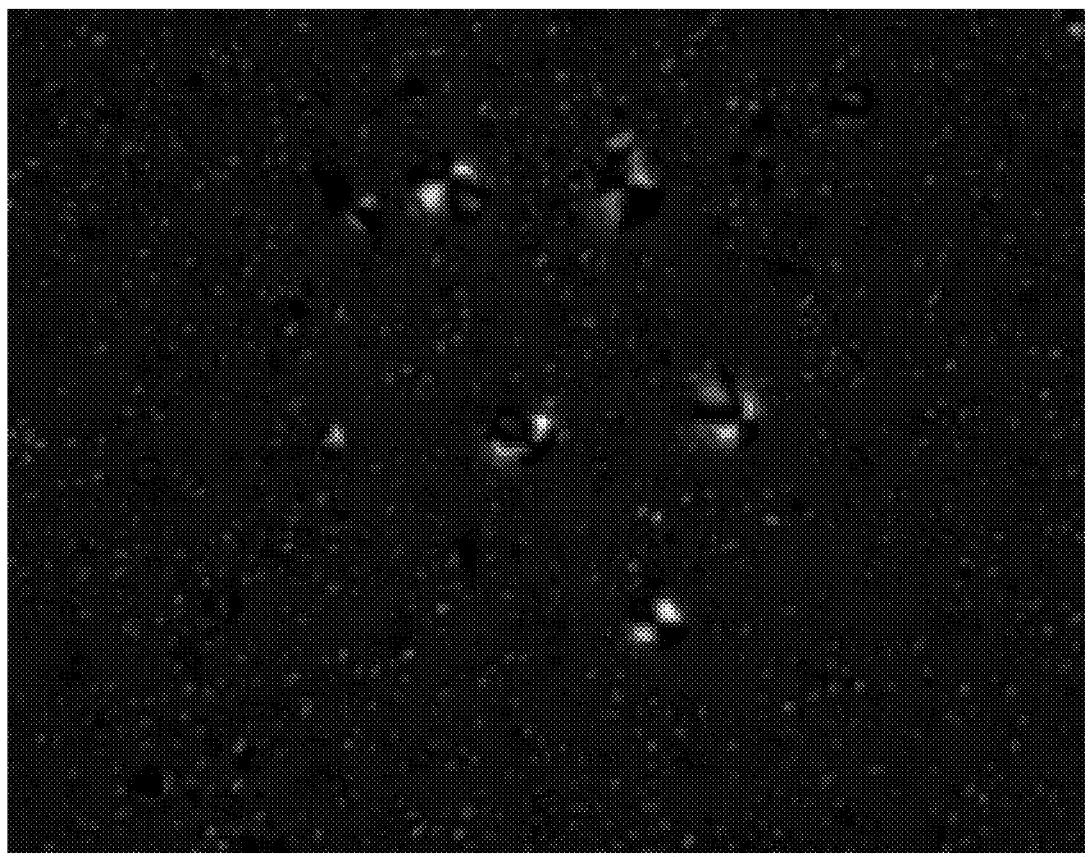
FIG. 7B depicts polarized light microscopy (400×) photographs of micronized AMIOCA® starch.
Figure 8A:
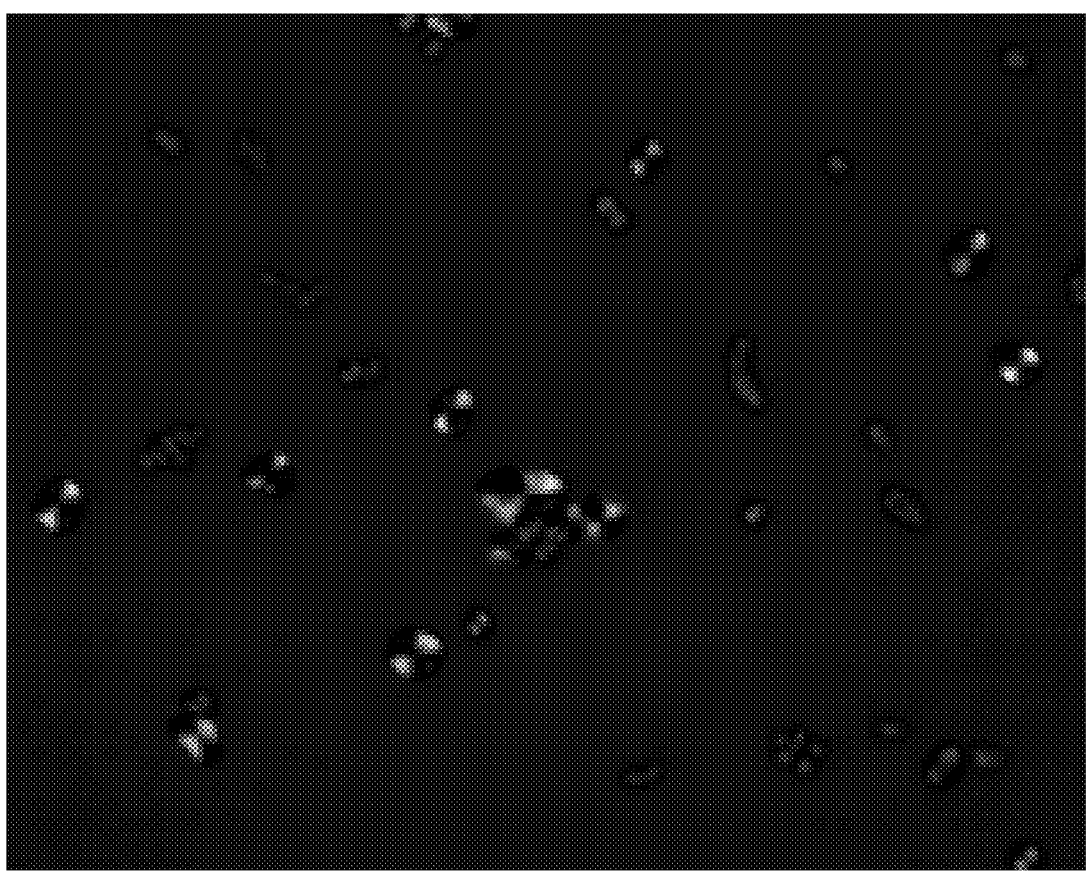
FIG. 8A depicts polarized light microscopy (400×) photographs of base granular HYLON® VII starch.
Figure 8B:
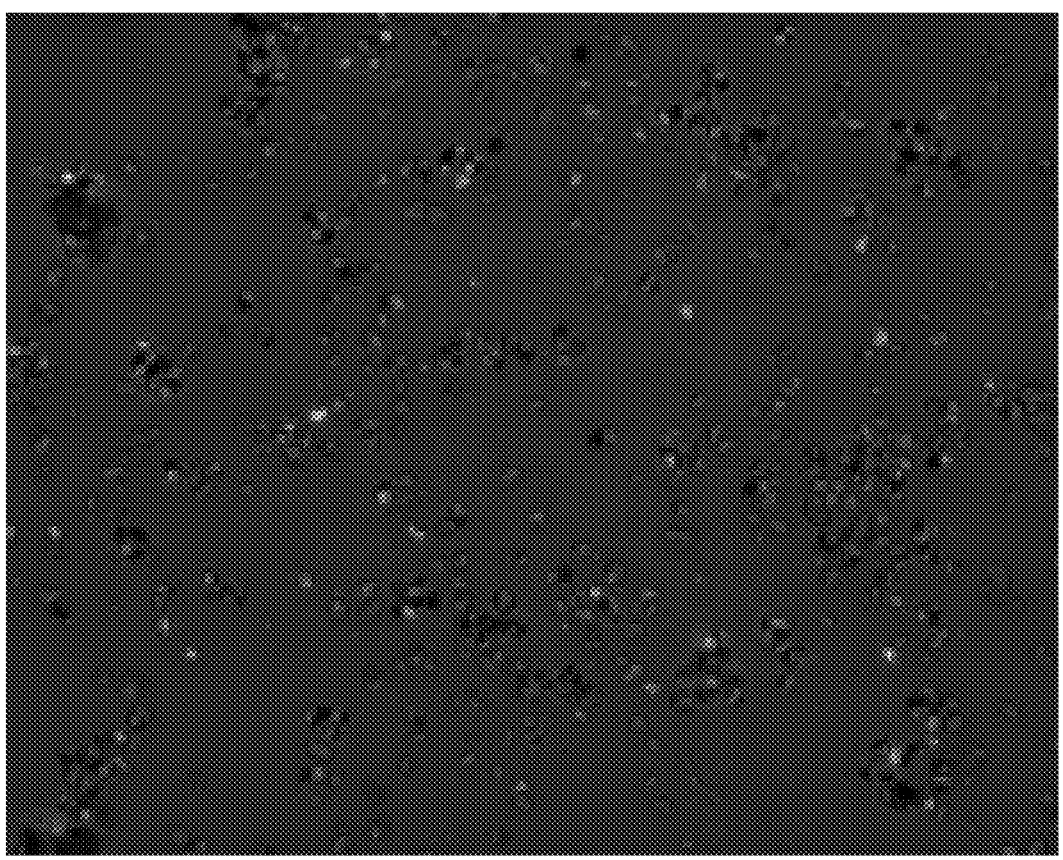
FIG. 8B depicts polarized light microscopy (400×) photographs of micronized HYLON® VII starch.
Figure 9A:
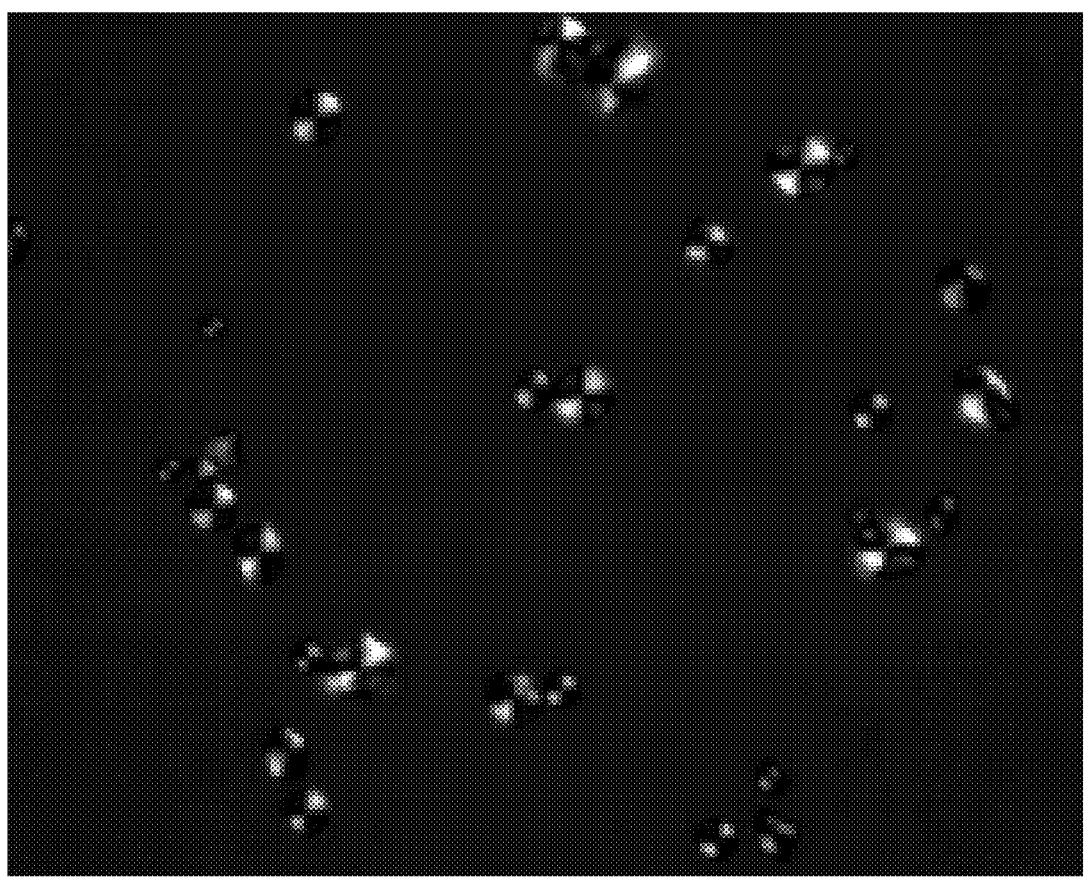
FIG. 9A depicts polarized light microscopy (400×) photographs of base granular MELOJEL® starch.
Figure 9B:
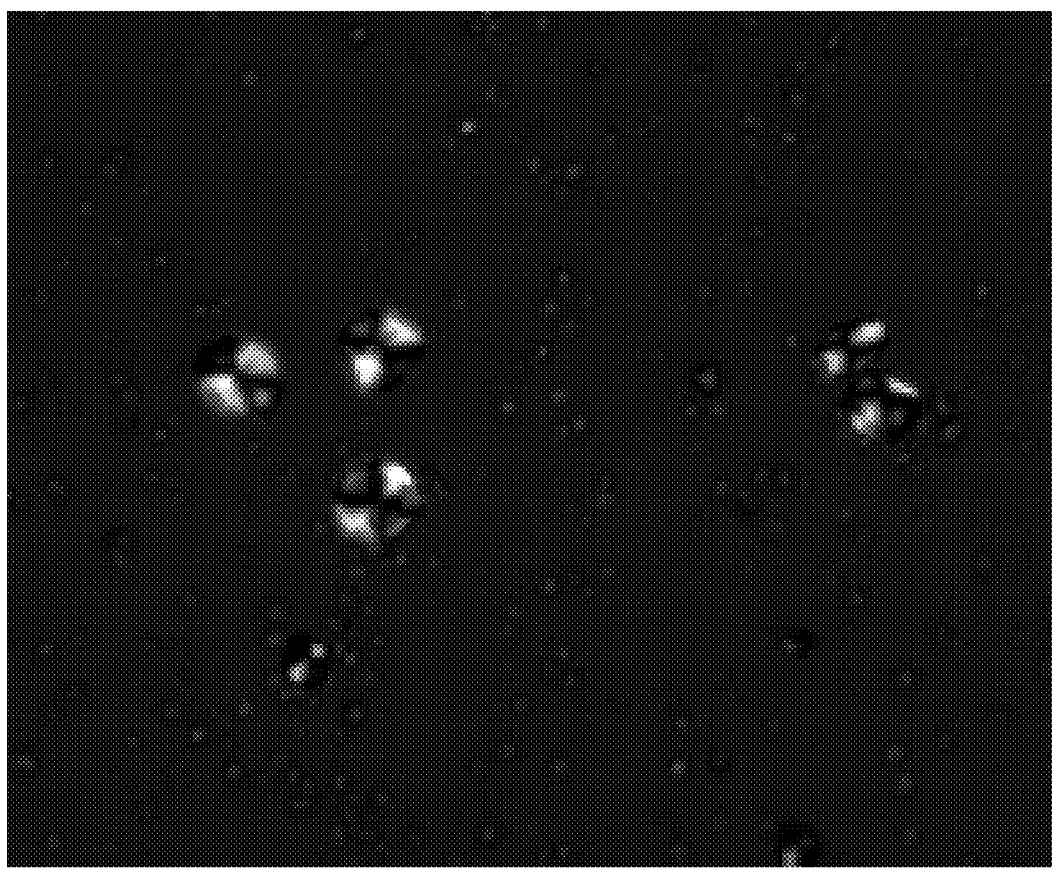
FIG. 9B depicts polarized light microscopy (400×) photographs of micronized MELOJEL® dent corn starch.

Retention of Crystallinity in Micronized Starches as Measured by Retention of Birefringence FIG. 7A (base granular AMIOCA® starch) vs. FIG. 7B (micronized AMIOCA® starch); FIG. 8A (base granular HYLON® VII starch) vs. FIG. 8B (micronized HYLON® VII starch); and FIG. 9A (base granular MELOJEL® starch) vs. FIG. 9B (micronized MELOJEL® starch) demonstrate that micronized starches retain most of the crystallinity of the granular starches from which they are derived, as analyzed using the procedure of Example 4.

Example 16

Gelatinization Temperature of Micronized Starches

Using the procedure of Example 5, the gelatinization temperature of the micronized starches was determined. Micronized AMIOCA® starch gelation began at approximately 65° C., close to the 65° C. gelation temperature of base granular AMIOCA® starch. Micronized HYLON® VII starch gelation began at approximately 72° C., lower than the 88° C. gelation temperature of the base granular HYLON® VII starch. Micronized MELOJEL® starch gelation began at approximately 65° C., close to the 65° C. gelation temperature of base granular MELOJEL® starch.

TABLE 3

| Sample | Gelatinization temp (native). | Gelatinization temp (micronized), |
|---|---|---|
| AMIOCA® starch | 65° C. | 65° C. |
| HYLON® VII starch | 88° C. | 72° C. |
| MELOJEL® starch | 66° C. | 66° C. |

Example 17

Heat of Enthalpy of Micronized Starches

Figure 10:
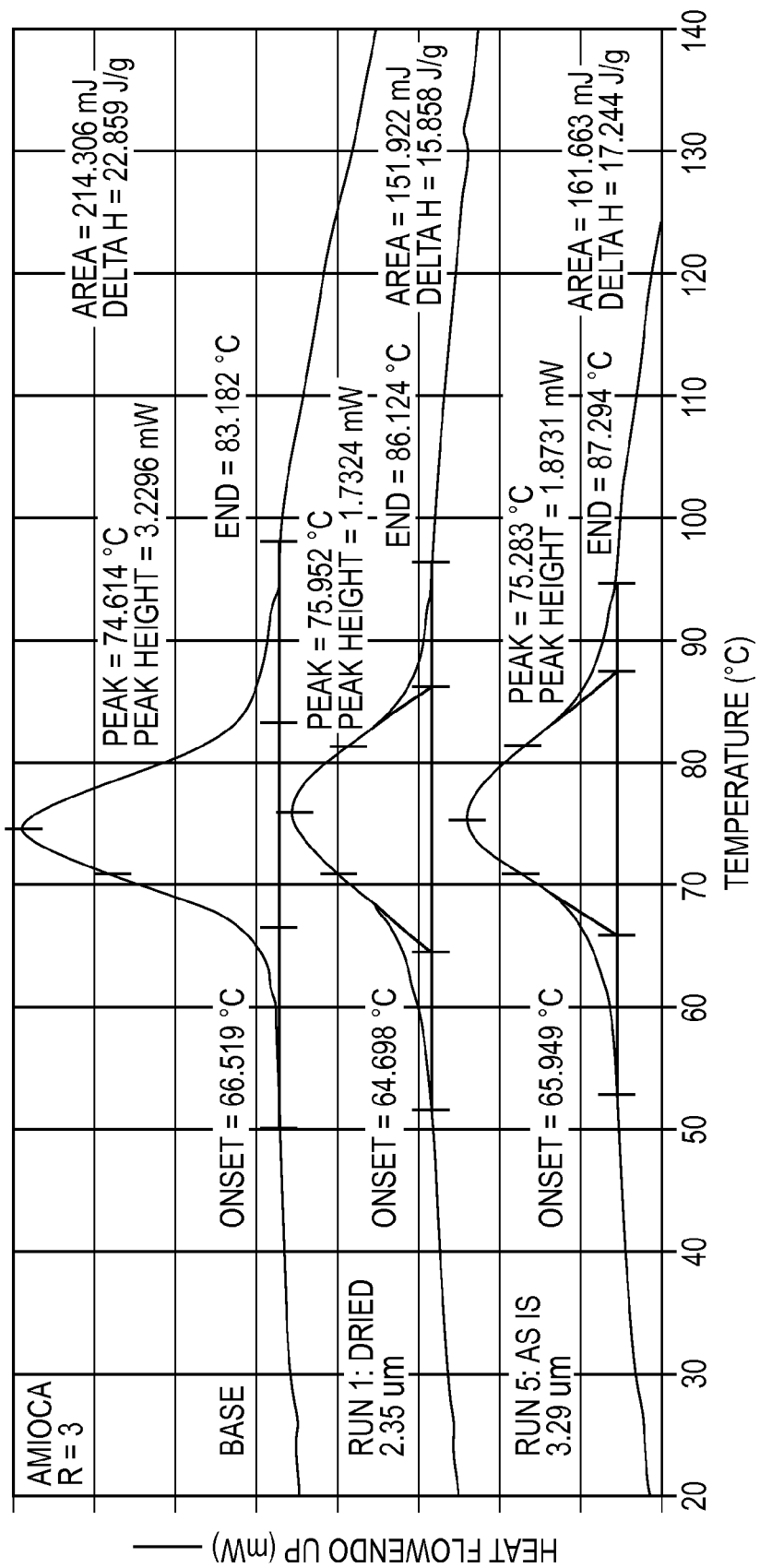
FIG. 10 depicts melting enthalpy of AMIOCA® base granular starch as compared to melting enthalpy of micronized AMIOCA® starch.
Figure 11:
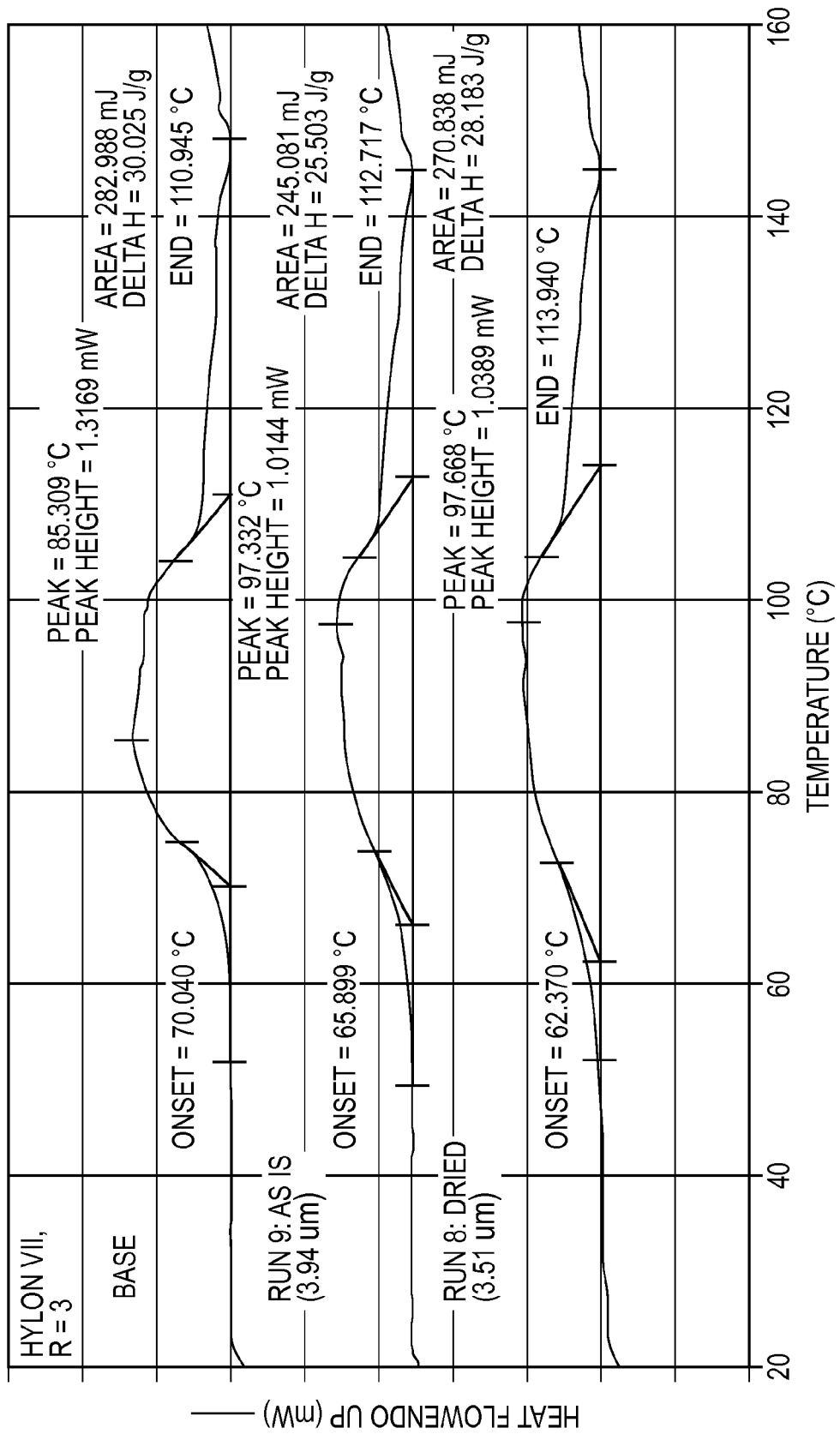
FIG. 11 depicts melting enthalpy of HYLON® VII base starch as compared to melting enthalpy of micronized HYLON® VII starch.
Figure 12:
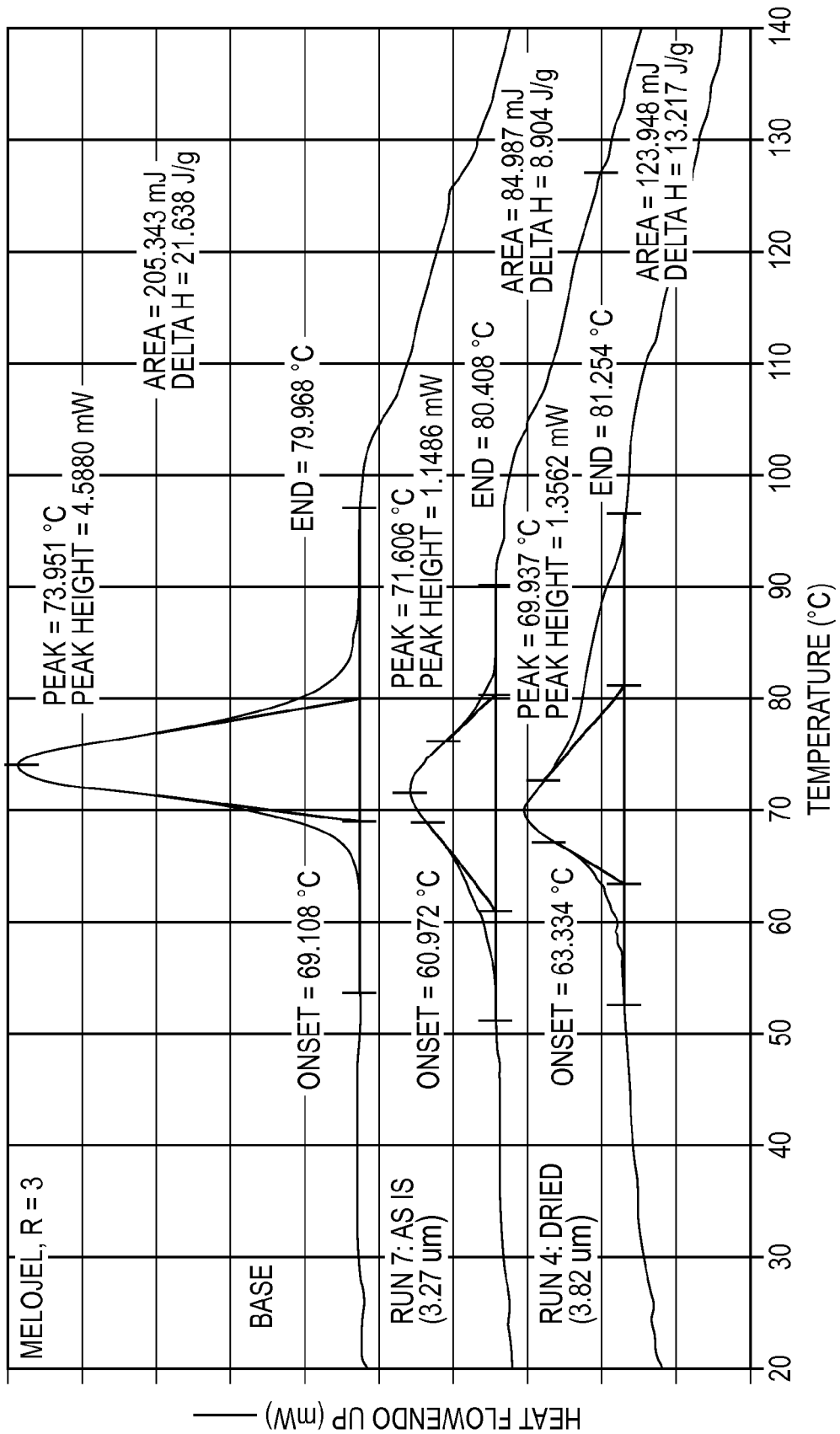
FIG. 12 depicts melting enthalpy of MELOJEL® base granular starch as compared to melting enthalpy of micronized MELOJEL® starch.

Using the protocol outlined in Example 6 above, the heat of enthalpy of the micronized starches was measured. These data are also shown in FIG. 10 (AMIOCA® starch); FIG. 11 (HYLON® VII starch), and FIG. 12 (MELOJEL® starch). Table 4 below demonstrates that micronized starches produced in accordance with Example 13 exhibit decreased heat of enthalpy as compared to base granular starches.

TABLE 4

| Starch | Onset Temp. To (° C.) | Peak Temp. Tg (° C.) | Peak Height (mW) | End Temp. (° C.) (J/g, db starch) | Area (mJ) | Enthalpy (ΔH) |
|---|---|---|---|---|---|---|
| AMIOCA ® starch (control) | 66.519 | 74.614 | 3.2296 | 83.182 | 214.306 | 22.859 |
| micronized AMIOCA ® starch) (dried) | 64.698 | 75.952 | 1.7324 | 86.124 | 151.922 | 15.858 |
| micronized AMIOCA ® starch (as is) | 65.49 | 75.283 | 1.8731 | 87.294 | 161.663 | 17.244 |
| HYLON ® VII starch (control) | 70.040 | 85.309 | 1.3169 | 110.945 | 282.988 | 30.025 |
| micronized HYLON ® VII starch (as is) | 65.899 | 97.332 | 1.0144 | 112.717 | 245.081 | 25.503 |
| micronized HYLON ® VII starch (dried) | 62.370 | 97.668 | 1.0389 | 97.668 | 270.838 | 28.183 |
| MELOJEL ® starch (control) | 69.108 | 73.951 | 4.5880 | 79.968 | 205.343 | 21.638 |
| micronized MELOJEL ® starch (as is) | 60.972 | 71.606 | 1.1486 | 80.408 | 84.987 | 8.904 |
| micronized MELOJEL ® starch (dried) | 63.334 | 69.937 | 1.3562 | 81.254 | 123.948 | 13.217 |

Example 18

Peak Viscosity Measurements of Micronized Starches

Using the experimental procedure set forth in Example 7 above and utilizing the micronized starches produced in accordance with Example 13, the peak viscosity was determined as shown in FIG. 13. This demonstrates that micronized AMIOCA® starch and MELOJEL® starch exhibit decreased peak viscosity as compared to the base granular starches.

Example 19

Particle Size and Size Distribution of Micronized Starches

Figure 15:
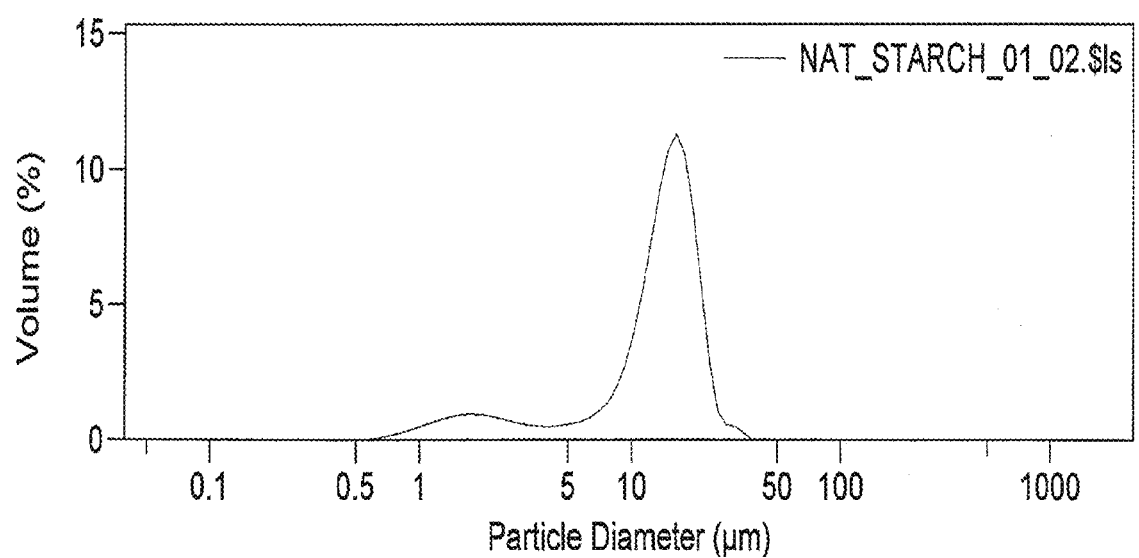
FIG. 15A depicts a particle size analysis of AMIOCA® starch before micronization.
FIG. 15B depicts a particle size analysis of AMIOCA® starch after micronization.
Figure 15:
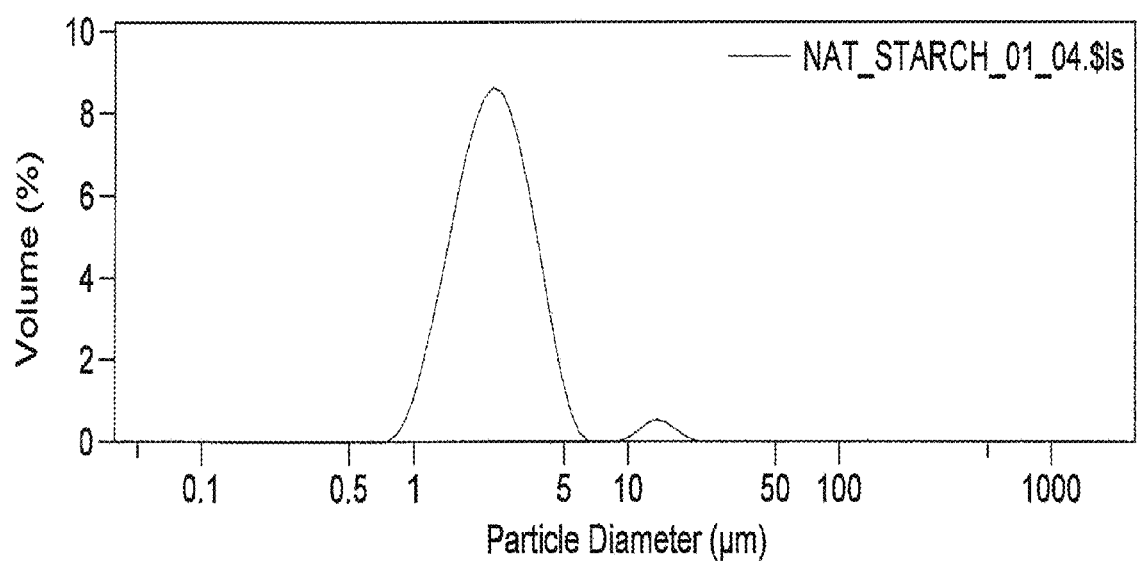

Using the particle size analysis outlined in Example 8 above, the micronized starches prepared in Example 13 were measured. The results are found in Table 1 and in FIGS. 15A, 15B, and 15C. Starch powder (about 0.1 g) was added into a 1 oz jar, and then was dispersed by agitation in distilled water. Starch suspension was then immediately introduced to the test chamber of the LS 13 320 for measurement. The sizes of base granular starch powders were also determined. Table 5 below gives the mean, median, and distribution of particle sizes for a variety of base granular starch powders.

TABLE 5

| Starches | Mean (μm) | Median (μm) | Distribution <25% | <50% | <75% |
|---|---|---|---|---|---|
| Rice | 7.6 | 6.1 | 4.0 | 6.1 | 8.9 |
| Normal Maize | 13.8 | 13.1 | 10.6 | 13.9 | 16.9 |
| Tapioca | 15.1 | 15.0 | 11.0 | 15.0 | 18.4 |
| Waxy Maize | 15.5 | 15.2 | 11.7 | 15.2 | 18.7 |
| Wheat | 16.1 | 15.3 | 9.5 | 15.3 | 21.5 |
| Barley | 17.7 | 17.6 | 13.5 | 17.5 | 21.6 |
| Banana | 26.9 | 26.7 | 17.0 | 26.7 | 35.8 |
| Pea | 33.9 | 31.3 | 25.9 | 31.3 | 39.0 |
| Potato | 41.2 | 39.5 | 28.1 | 39.6 | 53.6 |

Example 20

Measurement of the Crushing Strength of Tables Containing Micronized Starch

Figure 14A:
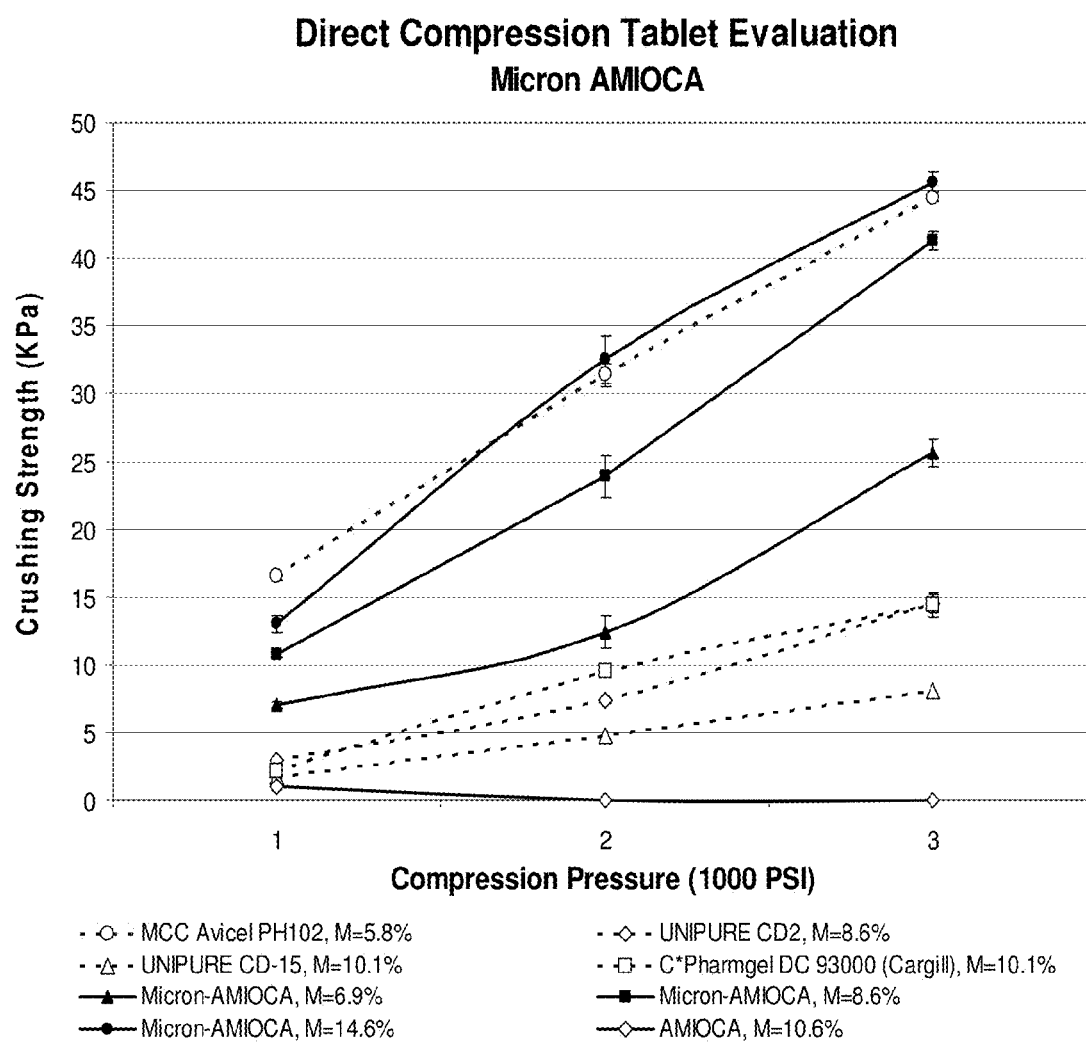
FIG. 14A depicts a comparison of crushing strength (KPa) of tablets manufactured with various industry standard components (microcrystalline cellulose, etc.) and with base and micronized AMIOCA® starch.
Figure 14B:
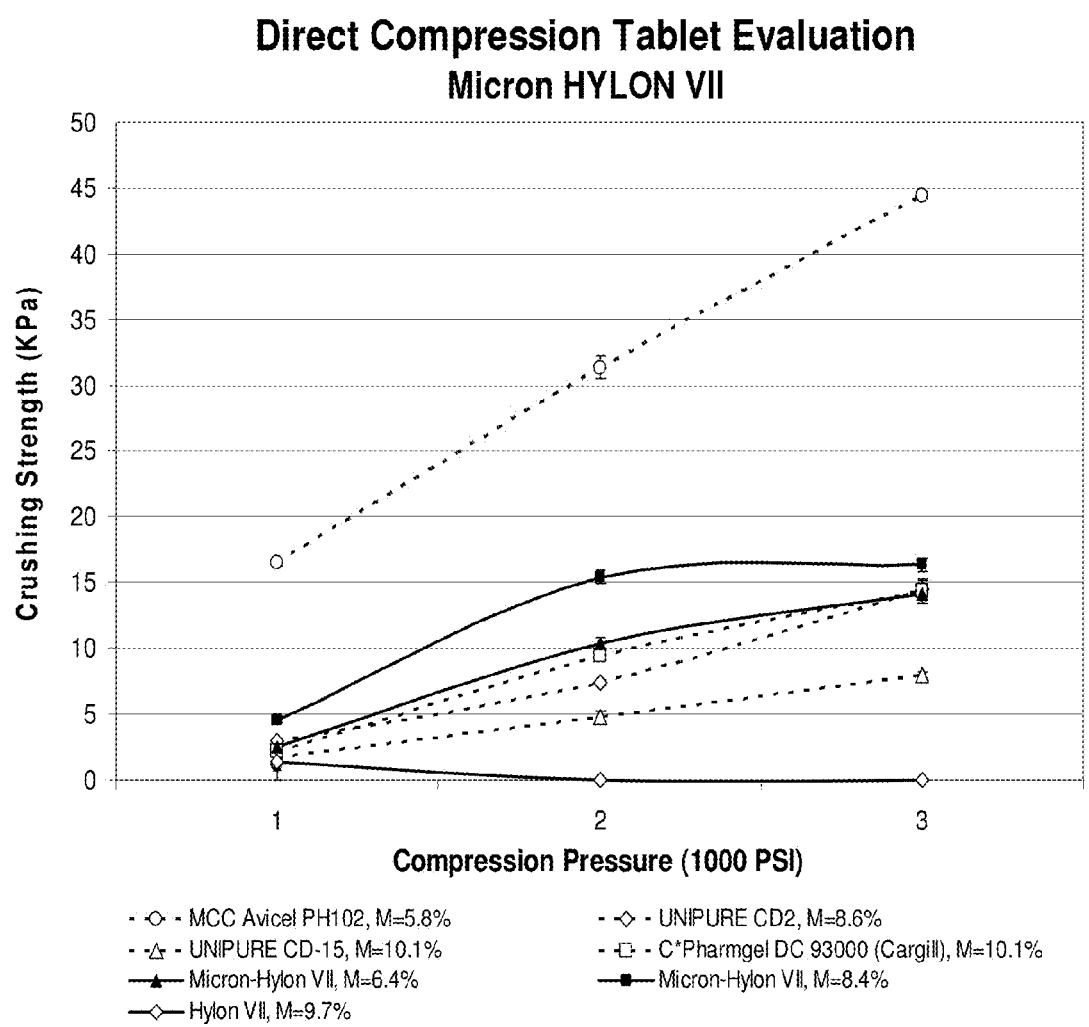
FIG. 14B depicts a comparison of crushing strength (KPa) of tablets manufactured with various industry standard components (microcrystalline cellulose, etc.) and with base and micronized HYLON® VII starch.
Figure 14C:
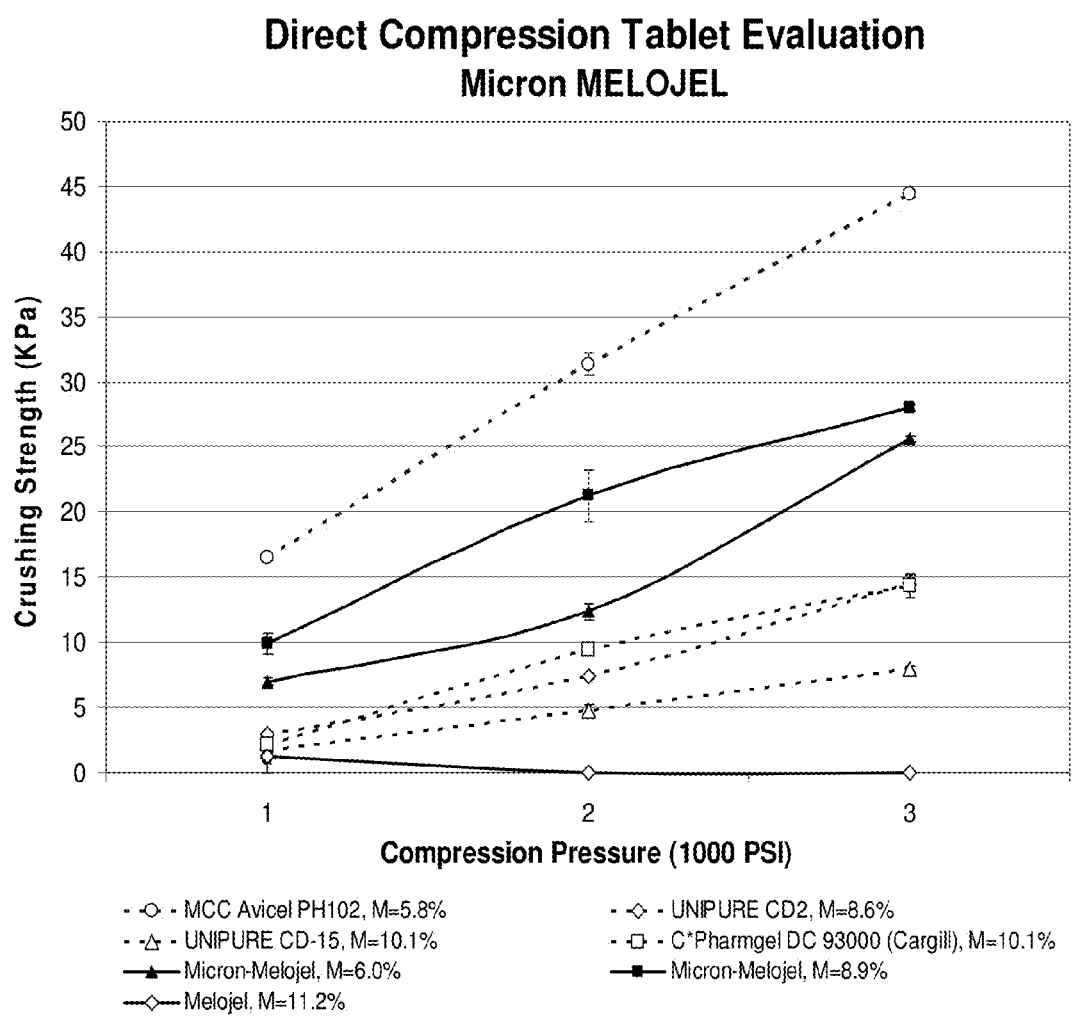
FIG. 14C depicts a comparison of crushing strength (KPa) of tablets manufactured with various industry standard components (microcrystalline cellulose, etc.) and with base and micronized granular starches (AMIOCA® starch; HYLON® VII starch; MELOJEL® starch).

Table 6 below illustrates the results of tablet preparation and crushing strength analysis undertaken in accordance with the procedure outlined in Examples 10 and 11 above. The micronized starches prepared in accordance with Example 13 were compared to various industry standard tablet materials (MCC AVICEL®; UNI-PURE® starch; etc.) The results are shown below, for tablets prepared using compression strength of 1000-3000 psi; and are further illustrated in FIG. 14A, FIG. 14B, and FIG. 14C.

TABLE 6

| Sample | Moisture (%) | 1000 psi (kPa) | 2000 psi (kPa) | 3000 psi (kPa) |
|---|---|---|---|---|
| MCC AVICEL PH 102 | 5.75 | 16.2 | 31.7 | 44.5 |
| UNI-PURE CD2 starch | 8.62 | 3.0 | 7.4 | 14.6 |
| UNI-PURE CD-15 starch | 10.05 | 1.7 | 4.6 | 8.0 |
| Starch 1500 Colorcon | 7.3 | 0 | N/A | N/A |
| C*Pharmgel DC 9300 (Cargill) | 10.1 | 2.2 | 9.4 | 14.4 |
| MELOJEL ® starch | 11.18 | 1.2 | N/A | N/A |
| AMOICA ® starch | 8.9 | 1.1 | N/A | N/A |
| HYLON ® VIII starch | 9.7 | 1.4 | N/A | N/A |
| MELOJEL ® micronized Starch | 6.03 | 6.7 | 12.5 | 25.6 |
| AMOICA ® micronized Starch | 6.85 | 5.5 | 12.0 | 19.6 |
| HYLON ® VII micronized Starch | 6.39 | 2.4 | 10.2 | 13.9 |
| MELOJEL ® micronized Starch | 14.13 | 9.5 | 28.3 | 23.7 |
| AMOICA ® micronized Starch | 14.58 | 12.0 | 32.8 | 45.2 |
| HYLON ® VII micronized Starch | 15.72 | 16.5 | 41.3 | 43.7 |

Example 21

Colloid Stability Analysis

Using the procedures of Examples 11 and 12, colloids were made from the micronized starches of Example 13. Micronized HYLON® VII starch showed much improved stability in ENSURE® from Abbott, while the base granular control precipitated out from ENSURE® after 8 hours.

Example 22

Measurement of the Degree of Polymerization (DP) of the Micronized Starches

The intrinsic viscosity [η] of starch solutions were measured at 23° C. by using a U-shape capillary viscometer (CANNON Instrument Co. 200W298) in 90% DMSO in water. The Solomon-Ciuta equation was used to calculate [η]: [η]=[2($\eta_{sp}$–ln $\eta_r$)]$^{0.5}$/c. The Mark-Houwink equation gave relation between intrinsic viscosity [η] and the molecular weight Mw: [η]=K(Mw)$^\alpha$. The value of the Mark-Houwink parameter K of 0.59 is taken from Millard et al. Cereal Chemistry, 1997, 74 (5), 687-691, which used light scattering methods to determine Mw. The value of the Mark-Houwink parameter c' of 0.31 is that of a compact hydrodynamic starch conformation. The degree of polymerization (DP) of each starch was calculated as: DP=(Mw–18)/162. Table 7 below illustrates the results of Mw and DP analysis undertaken in accordance with this procedure. The micronized starches prepared in accordance with Example 13.

TABLE 7

| Starch | run | [η] (mL/g) | Mw (10$^6$) | DP (10$^3$) |
|---|---|---|---|---|
| micronized AMIOCA ® starch) (dried) | 1 | 165 | 79 | 486 |
| micronized AMIOCA ® starch) (dried) | 2 | 169 | 84 | 519 |
| micronized MELOJEL ® starch (dried) | 3 | 184 | 111 | 688 |
| micronized MELOJEL ® starch (dried) | 4 | 168 | 83 | 515 |
| micronized AMIOCA ® starch (as is) | 5 | 199 | 144 | 888 |
| micronized MELOJEL ® starch (as is) | 6 | 155 | 64 | 397 |
| micronized MELOJEL ® starch (as is) | 7 | 144 | 51 | 314 |
| micronized HYLON ® VII starch (dried) | 8 | 84 | 9 | 55 |
| micronized HYLON ® VII starch (as is) | 9 | 89 | 10 | 65 |

Throughout this application, various publications are referenced. The disclosures of these publications in their entireties are hereby incorporated by reference into this application in order to more fully describe the state of the art as known to those skilled therein as of the date of the application described and claimed herein.

While particular embodiments of the present application have been illustrated and described, it would be obvious to those skilled in the art that various other changes and modifications can be made without departing from the spirit and scope of the application. It is therefore intended to cover in the application all such changes and modifications that are within the scope of this application.

What is claimed is:

1. A micronized starch granule with an average particle size as assessed by Polarization Intensity Differential Plus Electric Light Scattering of 1 μm to 5 μm and a degree of polymerization greater than 100, wherein the micronized starch retains at least 50% of the crystallinity as determined by X-ray diffraction of a base granular starch from which the micronized starch is derived.

2. The micronized starch granule of claim 1, wherein the micronized starch retains at least 60% of the crystallinity of the base granular starch from which the micronized starch is derived.

3. The micronized starch granule of claim 1, wherein the micronized starch retains between 50% and 90% of the crystallinity of the base granular starch from which the micronized starch is derived.

4. The micronized starch granule of claim 1, wherein the base granular starch from which the micronized starch is derived is a cereal starch.

5. The micronized starch granule of claim 4, wherein the base granular starch from which the micronized starch is derived is a corn starch.

6. The micronized starch of claim 1, wherein the melting enthalpy of the micronized starch as determined by differential scanning calorimetry is at least 50% of the melting enthalpy of the base granular starch from which the micronized starch is derived.

7. The micronized starch granule of claim 1, wherein a gelatinization temperature of the micronized starch granule is no more than 16° C. different than the gelatinization temperature of the base granular starch from which the micronized starch is derived, wherein the gelatinization temperature is the onset temperature of gelatinization when the starch first begins to swell.

8. The micronized starch granule of claim 1, wherein a peak viscosity as determined by Brabender viscoamylograph of the micronized starch granule is not greater than 90% of the peak viscosity of the base granular starch from which the micronized starch granule is derived.

9. The micronized starch granule of claim 1, wherein the degree of polymerization of the micronized starch is greater than 1,000.

10. The micronized starch granule of claim 1, wherein the degree of polymerization of the micronized starch is greater than 10,000.

11. The micronized starch granule of claim 1 having a moisture content of less than 5% based on total weight of the micronized starch.

* * * * *